(12) United States Patent
Lin-Shiau

(10) Patent No.: US 11,197,904 B2
(45) Date of Patent: Dec. 14, 2021

(54) PHARMACEUTICAL COMPOSITIONS FOR PREVENTIONS AND MANAGEMENTS OF DEMENTIA, INFECTIOUS DISEASES, CANCERS, PERIODONTITIS, DENTAL CARIES, DIABETES, OBESITY, OSTEOPOROSIS AND CHRONIC PAIN AND METHODS THEREOF

(71) Applicants: Shoei-Yn Lin-Shiau, Taichung (TW); Chung Shan Medical University, Taichung (TW)

(72) Inventor: Shoei-Yn Lin-Shiau, Taichung (TW)

(73) Assignees: Shoei-yn Lin-Shiau, Taichung (TW); Chung Shan Medical University, Taichung (TW)

( * ) Notice: Subject to any disclaimer, the term of this patent is extended or adjusted under 35 U.S.C. 154(b) by 266 days.

(21) Appl. No.: 16/252,697

(22) Filed: Jan. 20, 2019

(65) Prior Publication Data
US 2019/0224266 A1 Jul. 25, 2019

Related U.S. Application Data

(60) Provisional application No. 62/621,028, filed on Jan. 23, 2018.

(51) Int. Cl.
| | | |
|---|---|---|
| *A61K 36/82* | (2006.01) |
| *A61K 45/06* | (2006.01) |
| *A61P 31/04* | (2006.01) |
| *A61K 36/9066* | (2006.01) |
| *A61K 33/24* | (2019.01) |
| *A61K 33/243* | (2019.01) |

(52) U.S. Cl.
CPC .............. *A61K 36/82* (2013.01); *A61K 33/24* (2013.01); *A61K 33/243* (2019.01); *A61K 36/9066* (2013.01); *A61K 45/06* (2013.01); *A61P 31/04* (2018.01)

(58) Field of Classification Search
CPC .... A61K 2300/00; A61K 31/05; A61K 31/12; A61K 31/13; A61K 31/155; A61K 31/353; A61K 31/44; A61K 31/4706; A61K 31/5415; A61K 31/64; A61K 31/663; A61K 33/04; A61K 33/16; A61K 33/24; A61K 33/30; A61K 33/32; A61K 33/34; A61K 38/12; A61K 36/82; A61K 36/9066
See application file for complete search history.

(56) References Cited

U.S. PATENT DOCUMENTS 9,566,237 B2 * 2/2017 Mannino ................. A61P 37/06
2014/0094513 A1 4/2014 Lin-Shiau et al.

OTHER PUBLICATIONS

Claudio Franceschi et al., The Continuum of Aging and Age-Related Diseases: Common Mechanisms but Different Rates, Frontiers in Medicine, Mar. 12, 2018, pp. 1-23 (Article 61), vol. 5.
Tianlang Zhang et al., Comparative Epidemiological Investigation of Alzheimer's Disease and Colorectal Cancer: The Possible Role of Gastrointestinal Conditions in the Pathogenesis of AD, Frontiers in Aging Neuroscience, Sep. 28, 2018, pp. 1-12 (Article 176), vol. 10.
Tzeng Ns et al., Are Chronic Periodontitis and Gingivitis Associated with Dementia? A Nationwide, Retrospective, Matched-Cohort Study in Taiwan, Neuroepidemiology, Sep. 13, 2016, pp. 82-93, vol. 47(2).
Chang-Kai Chen el al., Association between Chronic Periodontitis and the Risk of Alzheimer's Disease: A Retrospective, Population-based, Matched-cohort Study, Alzheimer's Research & Therapy, 2017, pp. 1-7.
Lindsay Joy Spielman et al., Unhealthy Gut, Unhealthy Brain: The Role of the Intestinal Microbiota in Neurodegenerative Diseases, Neurochemistry International, 2018, pp. 149-163, vol. 120.
Elena Rybnikova, Brain, Antibiotics, and Microbiota—How Do They Interplay?, Journal of Neurochemistry, 2018, p. 208-210, vol. 146.
Vo Van Giau et al., Gut Microbiota and Their Neuroinflammatory Implications in Alzheimer's Disease, Nutrients, 2018, pp. 1-18.
Junges VM et al., Crosstalk between Gut Microbiota and Central Nervous System: A Focus on Alzheimer's Disease, Current Alzheimer Research, 2018, pp. 1179-1190, vol. 15(13).
Marta Sochocka et al., The Gut Microbiome Alterations and Inflammation-Driven Pathogenesis of Alzheimer's Disease—a Critical Review, Molecular Neurobiology, Jun. 23, 2018.
Anna B. Pritchard et al., Periodontitis, Microbiomes and Their Role in Alzheimer's Disease, Frontiers in Aging Neuroscience, Oct. 24, 2017, pp. 1-10 (Article 336), vol. 9.
Maite Solas et al., Inflammation and Gut-brain Axis Link Obesity to Cognitive Dysfunction: Plausible Pharmacological Interventions, Current Opinion in Pharmacology, 2017, pp. 87-92, vol. 37.
Mark Ide et al., Periodontitis and Cognitive Decline in Alzheimer's Disease, Plos One, Mar. 10, 2016, pp. 1-9.
Yu-Li Lin et al., Composition of Polyphenols in Fresh Tea Leaves and Associations of Their Oxygen-Radical-Absorbing Capacity with Antiproliferative Actions in Fibroblast Cells, Journal of Agricultural and Food Chemistry, 1996, pp. 1387-1394, vol. 44.
Jen-Kun Lin, Cancer Chemoprevention by Tea Polyphenols through Modulating Signal Transduction Pathways, Archives of Pharmacal Research, Oct. 2002, pp. 561-571, vol. 25(5).
Jen-Kun Lin et al., Mechanisms of Hypolipidemic and Anti-obesity Effects of Tea and Tea Polyphenols, Molecular Nutrition & Food Research, 2006, pp. 211-217, vol. 50.
Yea-Tzy Deng et al., EGCG Inhibits the Invasion of Highly Invasive CL1-5 Lung Cancer Cells through Suppressing MMP-2 Expression via JNK Signaling and Induces G2/M Arrest, Journal of Agricultural and Food Chemistry, 2011, pp. 13318-13327, vol. 59.

(Continued)

*Primary Examiner* — Aaron J Kosar

(57) ABSTRACT

The present invention relates to the area of pharmaceutical compositions. More particularly, the present invention relates to a series of pharmaceutical compositions (PTM) containing phyto-polyphenols (P), clinical drugs with selective targets (T) and a metal ions (M) and the methods thereof for use in prevention and therapy of infectious diseases, neurodegenerative diseases, dementia, diabetes, obesity, metabolic syndromes, osteoporosis, cancers and/or chronic pain.

11 Claims, 9 Drawing Sheets

(56) References Cited

OTHER PUBLICATIONS

HC Huang et al., Pu-erh Tea, Green Tea, and Black Tea Suppresses Hyperlipidemia, Hyperleptinemia and Fatty Acid Synthase through Activating AMPK in Rats Fed a High-fructose Diet, Food & Function, Feb. 2012, pp. 170-177, vol. 3(2).

Tsung-Yuan Yang et al., Weight Reduction Effect of Puerh Tea in Male Patients with Metabolic Syndrome, Phytotherapy Research, 2014, pp. 1096-1101, vol. 28.

Sung-Ho Chen et al., Involvement of Activating Transcription Factors JNK, NF-kappaB, and AP-1 in Apoptosis Induced by Pyrrolidine Dithiocarbamate/Cu Complex, European Journal of Pharmacology, 2008, pp. 9-17, vol. 594.

Sung-Ho Chen et al., Apoptosis of Cultured Astrocytes Induced by the Copper and Neocuproine Complex through Oxidative Stress and JNK Activation, Toxicological Sciences, 2008, pp. 138-149, vol. 102(1).

Po-Wen Cheng et al., Correlation of Increased Activities of Na+, K+-ATPase and Ca2+-ATPase with the Reversal of Cisplatin Ototoxicity Induced by D-methionine in Guinea Pigs, Hearing Research, 2005, pp. 102-109, vol. 205.

Chuan-Jen Hsu et al., Impact of Activities of Na+, K+-ATPase and Ca2+-ATPase in the Cochlear Lateral Wall on Recovery from Noise-induced Temporary Threshold Shift, Ann Otol Rhinol Laryngol, 2002, pp. 842-849, vol. 111.

Chang-Mu C et al., Characterization of Neurotoxic Effects of NMDA and the Novel Neuroprotection by Phytopolyphenols in Mice, Behavioral Neuroscience, Aug. 2010, pp. 541-553, vol. 124(4).

Chang-Mu Chen et al., Novel Regimen through Combination of Memantine and Tea Polyphenol for Neuroprotection against Brain Excitotoxicity, Journal of Neuroscience Research, 2008, pp. 2696-2704, vol. 86.

Chang-Mu Chen et al., Honokiol, a Neuroprotectant against Mouse Cerebral Ischaemia, Mediated by Preserving Na+, K+-ATPase Activity and Mitochondrial Functions, Basic & Clinical Pharmacology & Toxicology, 2007, pp. 108-116, vol. 101.

Shoei YN Lin Shiau et al., Tea Polyphenols Synergistic Enhancement of Antibacterial Effects of NaF on the Cultured *Streptococcus mutans*, Biomedical Journal of Scientific & Technical Research, 2018, pp. 1-7, vol. 6—Issue 2.

Leah E. Worton et al., Ectodermal-Neural Cortex 1 Isoforms Have Contrasting Effects on MC3T3-E1 Osteoblast Mineralization and Gene Expression, Journal of Cellular Biochemistry, 2017, pp. 2141-2150, vol. 118.

Jin Kyun Park et al., Expression of Cathepsin K and Tartrate-resistant Acid Phosphatase Is Not Confined to Osteoclasts but Is a General Feature of Multinucleated Giant Cells: Systematic Analysis, Rheumatology, May 14, 2013, pp. 1529-1533.

Wen-Pei Tseng et al., Activation of NMDA Receptor Partly Involved in Beta-bungarotoxin-induced Neurotoxicity in Cultured Primary Neurons, Neurochemistry International, 2003, pp. 333-344, vol. 42.

Wen-Pei Tseng et al., Long-term Lithium Treatment Prevents Neurotoxic Effects of Beta-bungarotoxin in Primary Cultured Neurons, Journal of Neuroscience Research, 2002, pp. 633-641, vol. 69.

Jiunn-Jye Chuu et al., Attenuation by Methyl Mercury and Mercuric Sulfide of Pentobarbital Induced Hypnotic Tolerance in Mice through Inhibition of ATPase Activities and Nitric Oxide Production in Cerebral Cortex, Archives of Toxicology, 2008, pp. 343-353, vol. 82.

Chun-Fa Huang et al., Neurotoxicological Effects of Cinnabar (a Chinese Mineral Medicine, HgS) in Mice, Toxicology and Applied Pharmacology, 2007, pp. 192-201, vol. 224.

Ting-Chao Chou, Drug Cobimination Studies and Their Synergy Quantification Using the Chou-Talalay Method, Cancer Research, Jan. 12, 2010, pp. 440-446, vol. 70(2).

\* cited by examiner

PHARMACEUTICAL COMPOSITIONS FOR PREVENTIONS AND MANAGEMENTS OF DEMENTIA, INFECTIOUS DISEASES, CANCERS, PERIODONTITIS, DENTAL CARIES, DIABETES, OBESITY, OSTEOPOROSIS AND CHRONIC PAIN AND METHODS THEREOF

CROSS-REFERENCE TO RELATED APPLICATION

This application claims the benefit of U.S. Provisional Patent Application No. 62/621,028 filed on Jan. 23, 2018, the entire content of which is hereby incorporated by reference.

FIELD OF THE INVENTION

The present invention relates to the area of pharmaceutical compositions. More particularly, the present invention relates to series of pharmaceutical compositions (PTM) having a polyphenols (P), a clinical drug with selective targets (T) and a metal ions (M). The present invention also relates to a method for use in antimicrobial effects against pathogens and/or for use in prevention and therapy of infectious diseases, neurodegenerative diseases, dementia, diabetes, obesity, metabolic syndromes, periodontitis, dental caries, osteoporosis, cancers and/or chronic pain.

BACKGROUND OF THE INVENTION

There are increasing rates in prevalence of many chronic diseases such as infectious diseases, neurodegenerative diseases (dementia, Parkinson's disease), obesity, diabetes, osteoporosis, cancers and chronic pain in the world[1,2]. Most of these diseases still have no curable therapeutic drugs. Recent studies suggest that the common risk factors involved in the pathogenesis of these diseases are[2-6]: (1) proinflammation (2) oxidative stress (3) mitochondrial dysfunction (4) infection (microbiome, dysbiosis) (5) immune system dysfunction. The most important issues are the oral- and gut-microbiome link to these non-curable diseases[5-12]. Because of antibiotic abuse, the drug resistant infectious diseases become an urgent issue to be overcome.

There are pleiotropic effects of phytopolyphenols, especially tea polyphenols (EGCG, theaflavins) and curcumin, which exerted antioxidant, antiinflammatory, antidiabetic, anti-obesity, anticancer, neuroprotection and antibacterial effects[13-18]. In addition, we have demonstrated that the divalent metal ions $Cu^{2+}$, $Mn^{2+}$, $Zn^{2+}$, $Sr^{2+}$ and selenite ($SeO_3^{-2}$) were active modulators on cell membrane $Ca^{2+}$ permeability, ion channels and ATPases, and thus exhibited profound effects on the release of neurotransmitters and influenced cell functions[19-22].

It has been a long time in exploration of the metal-based drugs. For instance, cisplatin is a Pt derivative used as an important anticancer drug. In addition, we have reported and got an American patent (Pub. No.: US 2014/0094513) about the synergistic effects of combined EGCG and memantine as a neuroprotectant against brain excitotoxicities (dementia) in mice[23-25].

Our strategy to combat the increasing prevalence and still no curable chronic diseases (dementia, diabetes, obesity, osteoporosis and cancer) especially the multidrug resistant infectious diseases is to develop the novel regimens with the pleiotropic pharmacological effects.

SUMMARY OF THE INVENTION

The present invention provides a series of pharmaceutical compositions for use in antimicrobial effects against pathogens and/or for use in prevention and therapy of infectious diseases, neurodegenerative diseases, dementia, diabetes, obesity, metabolic syndromes, periodontitis, dental caries, osteoporosis, cancers and/or chronic pain. These pharmaceutical compositions (PTM) comprise polyphenols (P), a clinical drug with selective targets (T) and a metal ions (M).

Based on the above findings, the polyphenols and the natural products are at least one selected from the group comprising tea polyphenols, curcumin, EGCG, theaflavin, berberine, apigenin, quercetin, tannin, catechin, chlorogenic acid, isoflavone, anthocyanidin, cocoa polyphenols, citrin, flavonoids tetramethylpyrazine, nordihydroguaiaretic acid and resveratrol etc.

According to the above, the clinical drug with selective target is at least one selected from the group comprising antibiotics, receptor agonists or antagonists, ion channel modulators, membrane ion transporters and mitochondrial functional modulators.

According to the above, the clinical drug with selective target is at least one selected from the group comprising NaF, memantine, metformin, thioridazine, chlorpromazine, tobramycin, rifampin, strepotomycin, isoniazide, verapamil, diltiazem, dithiothretol, dibucaine, digitonin, polymycin B, cisplatin, dequalinium, 4-hexylresorcinol, ursodeoxycholic acid, etidronate, glibenclamide and 3,4-diaminopyridine.

According to the above, the metal ions is at least one selected from the group comprising $Cu^{2+}$, $Mn^{2+}$, $VO_4^{2+}$, $Zn^{2+}$, $Sr^{2+}$, $SeO_3^{-2}$, $Ag^+$, Ge132 and RuR(Ruthenium red).

According to the above, the infectious pathogen is at least one selected from the group comprising *Porphyromonas gingivalis, Streptococcus mutans, E. coli, Pseudomonas aeruginosa, Bacillus subtilis, Staphytococcus aureus, Mycobacterium tuberculosis*, etc.

According to the above, the proportion between the concentration of the polyphenols and the clinical drug with selective target is 1:0.1-3, etc.

According to the above, an interaction between the polyphenols, the clinical drug with selective target and the metal ions leading to synergistic effects.

In one aspect, the invention provides a method for use in antimicrobial effects against pathogens and/or for use in prevention and therapy of infectious diseases, neurodegenerative diseases, dementia, diabetes, obesity, metabolic syndromes, osteoporosis, periodontitis, dental caries, cancers and/or chronic pain, comprising a polyphenols, a clinical drug with selective targets and a metal ion, wherein an interaction between the polyphenols, the clinical drug with selective targets and the metal ions leading to synergistic effects.

According to the above, the polyphenols are at least one selected from the group comprising tea polyphenols, curcumin, EGCG, theaflavin, apigenin, berberine, quercetin, tannin, catechin, chlorogenic acid, isoflavone, anthocyanidin, cocoa polyphenols, citrin, flavonoid and resveratrol etc.

According to the above, the clinical drug with selective target is at least one selected from the group comprising receptor agonists or antagonists, ion channel modulators, membrane ion transporters, mitochondrial functional modulators, immune modulators and antibiotics.

According to the above, the clinical drug with selective target is at least one selected from the group comprising NaF, memantine, metformin, thioridazine, chlorpromazine, etidronate, clodronate, glibenclamide, 3,4-diaminopyrine, verapamil, diltiazem, dithiothreitol, dibucaine, digitonin, polymycin B, tobramycin, rifampin, streptomycin, cisplatin, dequalinium, 4-hexylresorcinol, ursodeoxycholic acid, etidronate, glibenclamide and 3,4-diaminopyridine etc.

According to the above, the metal ions is at least one selected from the group comprising $Cu^{2+}$, $Mn^{2+}$, $VO_4^{2+}$, $Zn^{2+}$, $Sr^{2+}$, $SeO_3^{-2}$, $Ag^+$, Ge132 and RuR.

According to the above, the infectious pathogen is at least one selected from the group comprising Porphyromonas gingivalis, Streptococcus mutans, E. coli, Pseudomonas aeruginosa, Bacillus subtilis and Staphytococcus aureus, MRSA and Mycobacterium tuberculosis.

According to the above, the proportion between the concentration of the polyphenols and the clinical drug with selective target is 1:0.1-3.

The foregoing and other features or advantages of the present invention disclosure will be more readily appreciated by one of ordinary skilled in the art from the following figures, embodiments and descriptions.

BRIEF DESCRIPTION OF THE DRAWINGS

Some embodiments of the invention are herein described with reference to the accompanying drawings. With specific reference to the drawings in detail, it is emphasized that the particulars shown are by way of example and for purposes of illustrative discussion of embodiments of the invention.

DETAIL DESCRIPTION OF THE INVENTION

Figure 1:
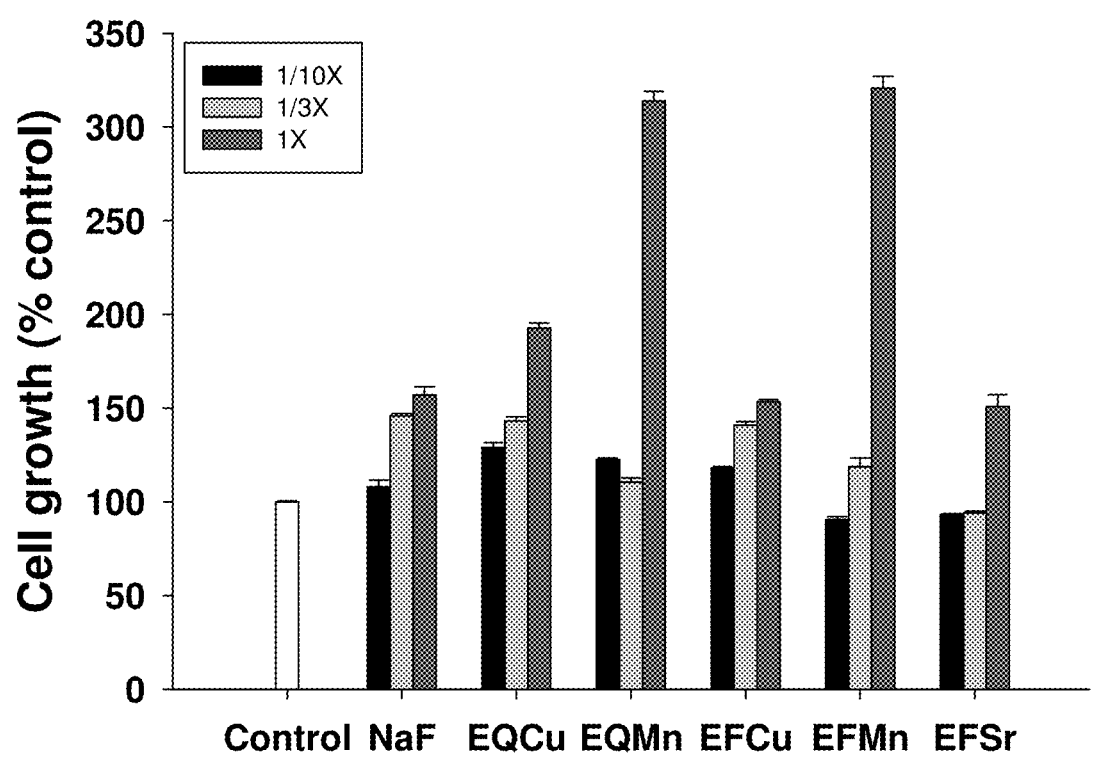
FIG. 1 shows that novel regimens enhancing the growth of Lactobacillus reuteri.
Figure 2A:
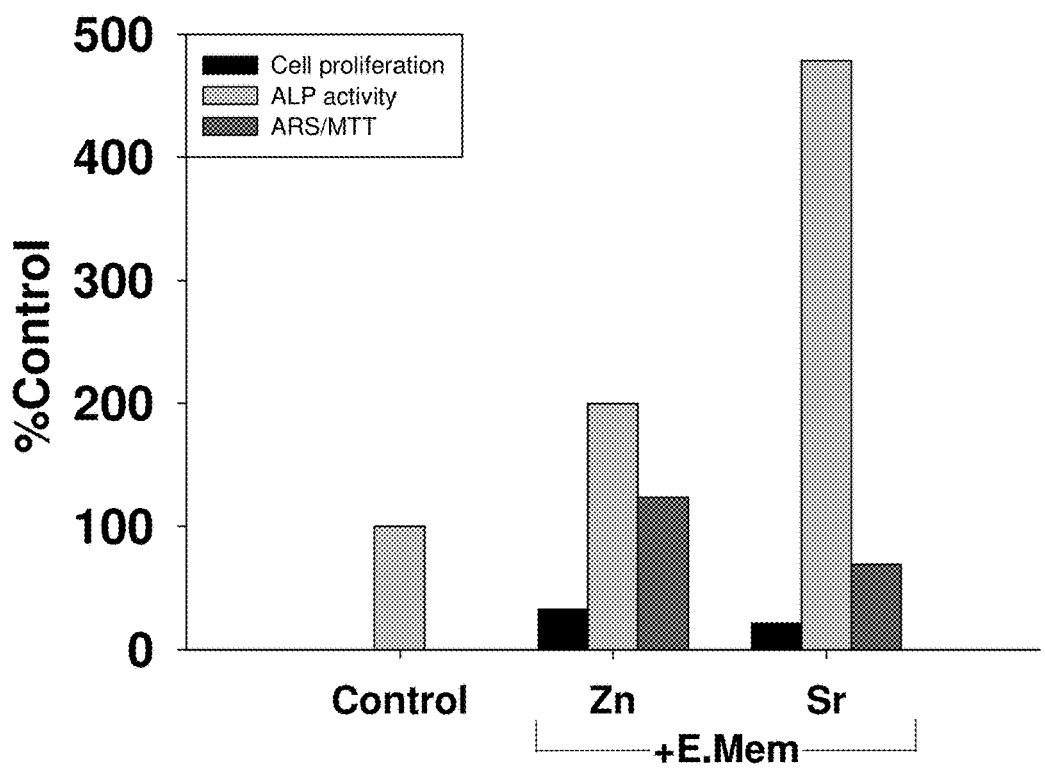
FIG. 2A shows that novel regimens increased alkaline phosphatase(ALP) and the ARS mineral contents of the cultured preosteoblast MC3T3-E1 cells.
Figure 2B:
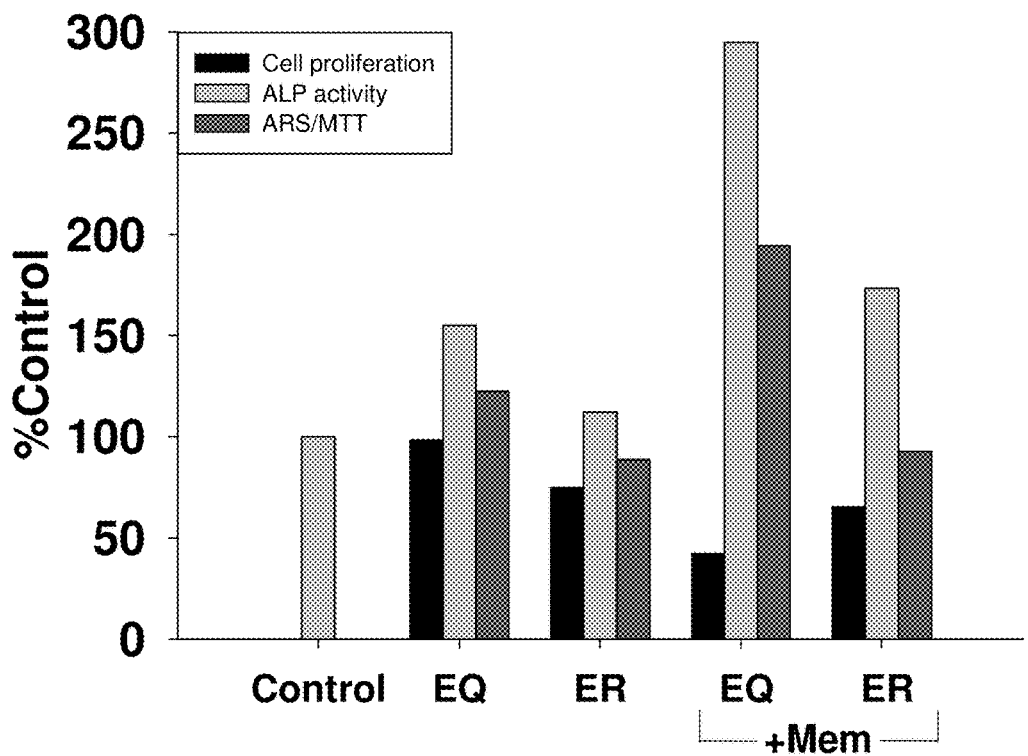
FIG. 2B shows that novel regimens increased alkaline phosphatase(ALP) and the ARS mineral contents of the cultured preosteoblast MC3T3-E1 cells.
Figure 2C:
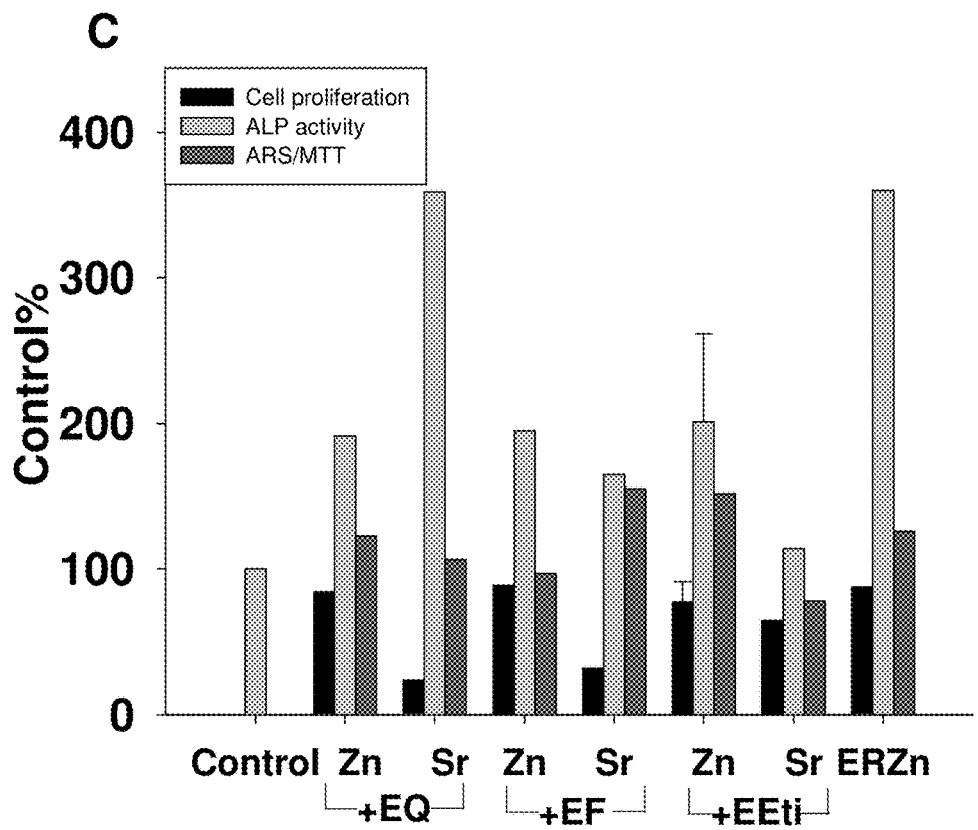
FIG. 2C shows that novel regimens increased alkaline phosphatase(ALP) and the ARS mineral contents of the cultured preosteoblast MC3T3-E1 cells.
Figure 2D:
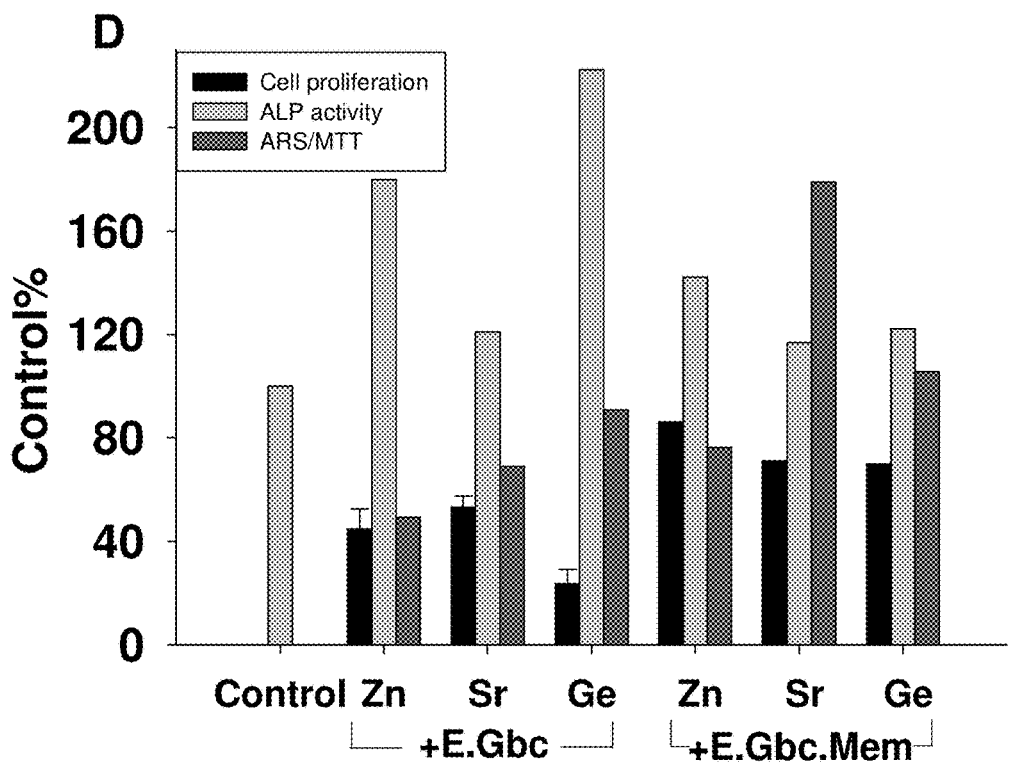
FIG. 2D shows that novel regimens increased alkaline phosphatase(ALP) and the ARS mineral contents of the cultured preosteoblast MC3T3-E1 cells.
Figure 2E:
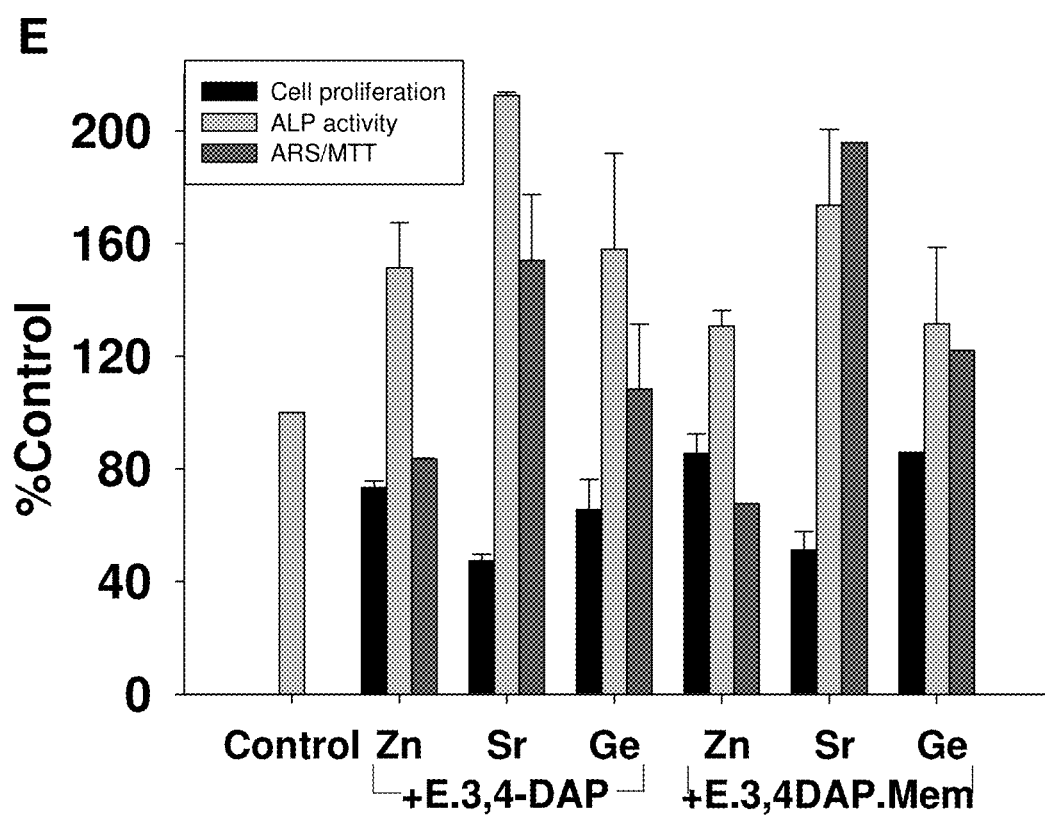
FIG. 2E shows that novel regimens increased alkaline phosphatase(ALP) and the ARS mineral contents of the cultured preosteoblast MC3T3-E1 cells.
Figure 3A:
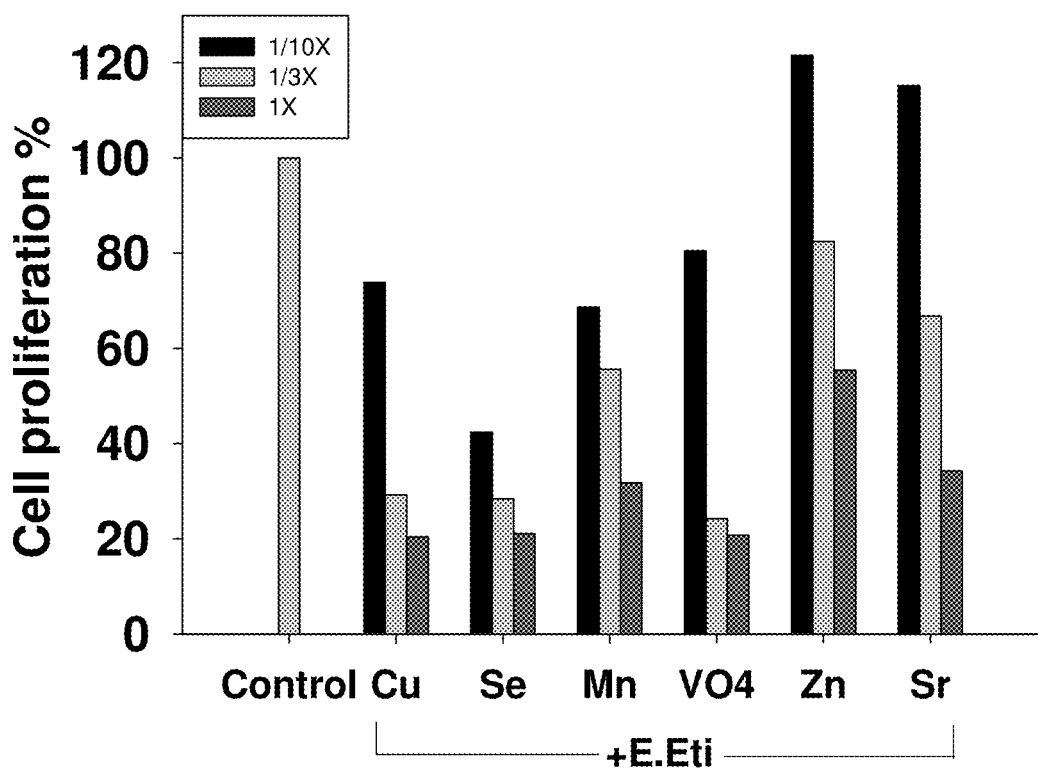
FIG. 3A shows the decreased tartrate-resistant acid phosphatase, (TRAP) activities of the novel regimens on the cultured preosteoclast RAW cells.
Figure 3B:
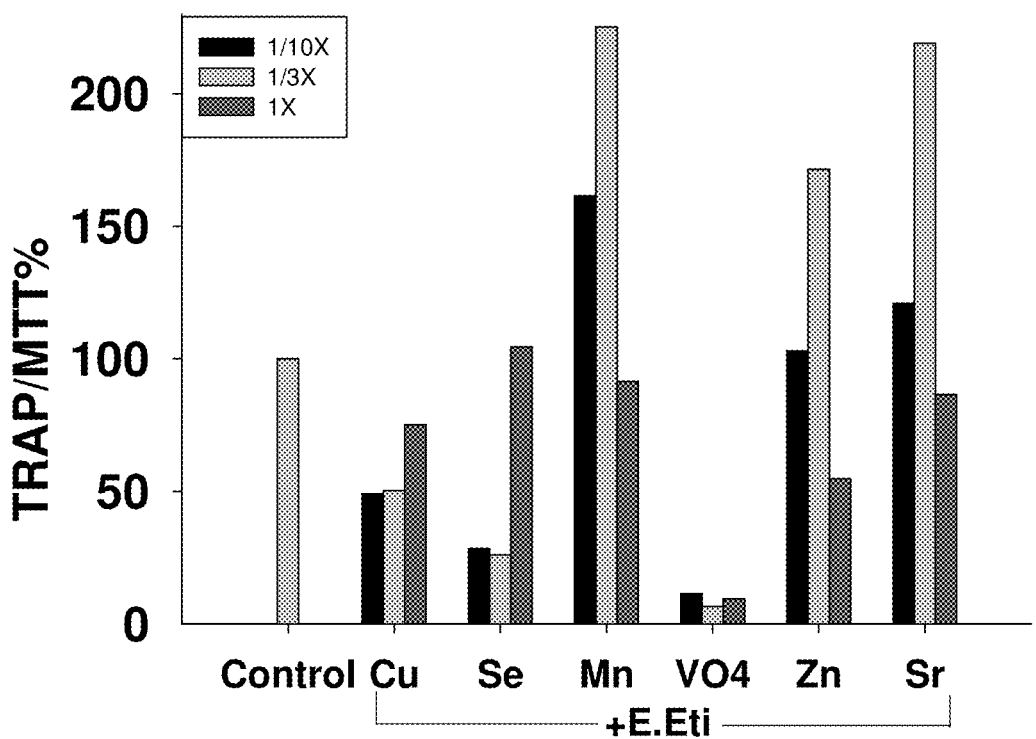
FIG. 3B shows the decreased tartrate-resistant acid phosphatase, (TRAP) activities of the novel regimens on the cultured preosteoclast RAW cells.
Figure 3C:
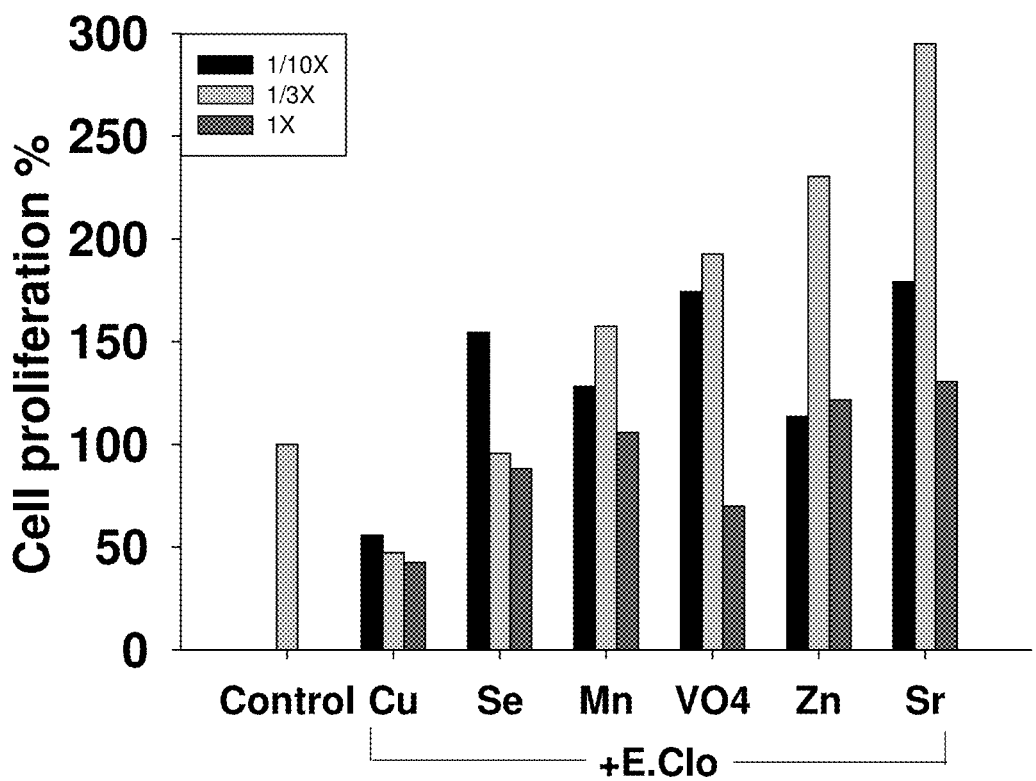
FIG. 3C shows the decreased tartrate-resistant acid phosphatase, (TRAP) activities of the novel regimens on the cultured preosteoclast RAW cells.
Figure 3D:
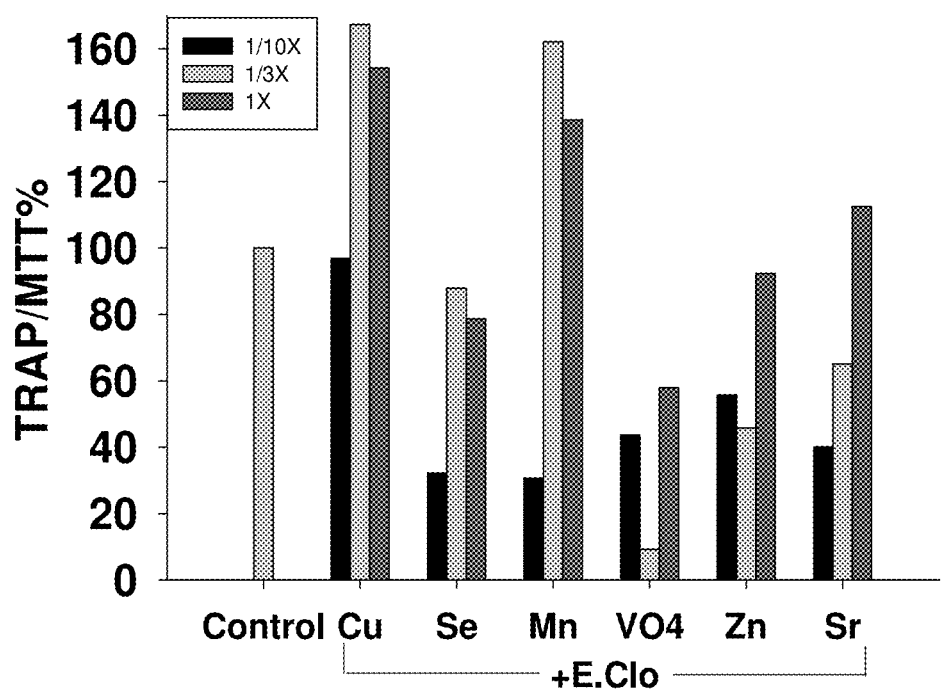
FIG. 3D shows the decreased tartrate-resistant acid phosphatase, (TRAP) activities of the novel regimens on the cultured preosteoclast RAW cells.

Disclosed are methods and compositions for providing a series of pharmaceutical compositions and use thereof. The invention will be able to be practiced by one skilled in the art that references to the following embodiments and descriptions.

Based on the major common risk factors (inflammation, oxidative stress, mitochondrial metabotic dysfunction, immune dysfunction and infection) involved in the pathogenesis of the above mentioned diseases[1-6], we have developed the novel regimens, PTM, with the advantage of their chemical complex formations of polyphenols and metals and pharmacological interactions, leading to the synergistic effects among them (anti-oxidant, anti-inflammatory, anti-microbial and neuroprotection)[23-25]; P, phytopolyphenols; T, clinical drugs with selective targeting such as receptor agonists or antagonists, ion channel modulators, membrane ion transporters, mitochondrial functional modulators, antibiotics etc.; M, metals such as $Cu^{2+}$, $Mn^{2+}$, $Zn^{2+}$, $VO_4^{2+}$, $Sr^{2+}$, $SeO_3^{-2}$, $Ag^+$, Ge132, ruthenium red etc.

Culture of Pathogens

The anaerobic pathogens, Streptococcus mutans (S.m., UA159) and Porphyromonas gingivalis (P.g.) were cultured in Brain heart infusion broth (BHI, Becton Dickinson, Sparks, Md.) and Wilkins-Chalgren Anaerobe Broth respectively at 37±0.5° C. in the anaerobic chamber containing 10% $H_2$, 5% $CO_2$ and 85% $N_2$, (Forma Scientific Inc., Marietta, Ohio, USA)[26].

The other four kinds of pathogens including E. coli, Pseudomonas aeruginosa (P.a.), Bacillus subtilis (B.s.) and Staphylococcus aureus (S.a) and the probiotic Lactobacillus reuteri (L.r.) were cultured aerobically at 37±0.5° C.

Anti-Microbial Effects of Drugs on the Proliferation of Pathogens

The proliferation rate of the cultured pathogens was measured by Elisa reader at optical density 600 nm (OD600). After 16 hour culture, the OD600 value of cultured pathogen was adjusted to about 0.55, which accounted the bacterial concentration about $1.7 \times 10^9$ CFU/ml. The effects of the drugs on the proliferation of the bacteria were evaluated by the changes of OD600 after addition various concentrations of drugs (10 µl/well) to 90 µl/well of the cultured bateria diluted with cultured broth by $10^6$ fold at $1.7 \times 10^3$ CFU/ml in 96 well microplates. The drug effects were evaluated after 24 h incubation with the bacteria by the changes of OD600 and then calculated as percentage of the control treated with vehicle saline. The experiments were carried out in triplicate. The antibacterial effects of the drugs were quantitatively by the concentration inhibition curves and calculated the concentration of each drug for 50% of inhibition ($IC_{50}$)[26].

Cell Culture

Cell culture medium (RPMI) and supplements were purchased from Sigma (St. Louise, USA). All culture media were supplemented with heat inactivated FBS (JRH Biosciences or Hyclone, Thermo Scientific).

OECM-1(oral squamous cell carcinoma cell), SG(gingival epithelial cells), RAW(preosteocast) and SHSY5Y(neuroblastoma) were cultured in $CO_2$(5%) incubate 37° C. MC3T3-E1(preosteoblast) cells were cultured in growth media (α-MEM with 10% FBS, 2 mM L-glutamine and 20 mM HEPES) supplemented with 10 mM β-glycerophosphate and 50 mg/L ascorbic acid. All cells were cultured at 37° C. and 5% $CO_2$.

Alkaline Phosphatase Assay and Alizarin Red Mineral Contents Detection

Akaline phosphatase (ALP) activity of MC3T3-E1 cell were measured by the reaction product nitrophenol of the substrate 8 mM PNPP(P-nitro-phenyl phosphate) with ALP in the $Na_2CO_3$ buffer (pH10) at 37° C. for 30 min and quantified by OD405 nm[27].

Mineral contents of MC3T3-E1 cells was measured by the reaction with Alizarin Red (ARS) and measured OD562 nm.

Tartrate-Resistant Acid Phosphatase (TRAP) Assay

TRAP activity of RAW cells was measured by the production of p-nitrophenol after the substrate 8 mM PNPP (P-nitrophenyl-phosphate) hydrolyzed by TRAP in 0.1 M Na acetate (pH5.7) with 40 mM Na tartrate. The absorbance at 405 nm was determined after incubation at 37° C. for 30 min[28].

Neuroprotection of Drugs Against $H_2O_2$ Oxidative Cytotoxicity on Cultured Neuroblastoma Cells (SHSY5Y)

The cytotoxic effects of the control $H_2O_2$ at 0.5, 1 and 3 mM on SHSY5Y cells at 37° C. for 24 hs, were assayed by MTT test and estimated as % control cells treated with vehicles[29,30].

Neuroprotection of drugs was detected by the addition of the drugs 10 min or 30 min after 1 mM $H_2O_2$ application, and cell survivals measured by MTT test were compared with that treated with 1 mM $H_2O_2$ alone.

TruScan Photobeam Tracking

TruScan photobeam tracking are used to record behavior (walking distance in margin and center area, number of times for jumping, rest time and total time of walking) of mice to compute emotional alteration as we previously reported[31,32]. The tracking activity of depressed mice exhibits limited center area walking distance; while normal mice distributes equally in margin and center area walking distance. Additionally, the tally of jumping and standing show the exploration and curious behavior of normal mice.

Preparation of the Drugs (1) Preparation of Tea Polyphenols (TP):

TP were isolated by the methods described in our previous reports[13,15]. One hundred grams of green tea or black tea (produced by Wangs' Tea Enterprise Co., Ltd., Taipei, Taiwan), was suspended in 1 L of distilled water at 75° C. for 30 min; then the supernatant was collected. This step was repeated three times. The supernatant were filtered to eliminate chlorophylls and undissolved particle. The total aqueous layers were concentrated to 0.5 L under reduced pressure using a rotatory vacuum evaporator. The concentrated solution was extracted with an equal volume of chloroform three times to eliminate caffeine and pigments. The remaining aqueous phase was then extracted with an equal volume of ethyl acetate three times to extract tea polyphenols. The TP in ethyl acetate was combined and evaporated in vacuum. The residue was dissolved in a small volume of distilled water and freeze-dried. This goldbrown solid matter was called tea polyphenols.

(2) Purified curcumin was purchased from Merck Co. (German), memantine(Mem), metformin(MF), etidronate(Eti), thioridazine(TRZ), chlorpromazine(CPZ), and ruthenium red(RuR) were all from Sigma Chemical Company (USA).

(3) Assessments of the Interactions in Antimicrobial Potencies of Drug Combinations:

The potencies of antimicrobial effect of various drug combinations as compared with that of drug alone were assessed by combination index (CI)[33].

$$CI = \frac{(IC_{50})_1 \text{ in combination}}{(IC_{50})_1 \text{ alone}} + \frac{(IC_{50})_2 \text{ in combination}}{(IC_{50})_2 \text{ alone}} + \frac{(IC_{50})_3 \text{ in combination}}{(IC_{50})_3 \text{ alone}}$$

$CI < 1$, synergism; $CI = 1$, addition; $CI > 1$, antagonism $$\text{Potency ratio(fold)} = \left( \frac{(IC_{50})_1 \text{ alone}}{(IC_{50})_1 \text{ in combination}} + \frac{(IC_{50})_2 \text{ alone}}{(IC_{50})_2 \text{ in combination}} + \frac{(IC_{50})_3 \text{ alone}}{(IC_{50})_3 \text{ in combination}} \right) \times \frac{1}{3}$$

STATISTICS

Results for each experiment were represented as mean±SEM. One way ANOVA followed by a post-hoc t test was used to evaluate differences between the groups. The level of significance was defined as $p<0.05$.

EXAMPLES

1. Antibacterial Effects of Polyphenols and Metals Either Alone or in Combination As shown on Tables 1A and 1B, phyto-polyphenols (EGCG, green tea polyphenols, curcumin) exhibited pleiotropic inhibitory effects on the proliferation of various cultured pathogens (P.g., UA159, P.a., S.a.) but not cinnamon. The combination of polyphenol and metals synergistically inhibited bacterial growth more than 10 fold as revealed by $IC_{50}$ of metals (mM) (Table 1C). Cinnamon-metal compounds still had no effects on bacteria growth except that cinnamon-RuR compounds synergistically inhibited P.g. and P.a. by 2.6 and 1.3 fold respectively as estimated by their decreased $IC_{50}$.

2. Antibacterial Effects of Various Drugs and Natural Compounds Studied in This Report:

As shown on Table.2A, among the repurposing drugs studied, dequalinium, thioridazine and chlorpromazine possessed antibacterial effects much more than the others (NaF, 4-hexyl-resorcinol, memantine, metformin, etidronate and quinine). The natural products (berberine, lysozyme, quercetin, tetramethylpyrazine and nordihydroguaiaretic acid) were also weak by themselves in anti-bacterial effects (Table 2B). However, the antibiotics (tobramycin, rifampin and streptomycin) were very potent anti-bacterial effects (Table 3A), but neither nystatin nor isoniazid had these effects alone (Table 3A). The polypeptides (polyarginine, protamine, polylysine, Arg-Phe) and toxin peptides (notexin, cobra cardiotoxin, cobra phospholipase $A_2$ and α-bungarotoxin) were also weak in antibacterial effects except some of these peptides inhibited P.g. growth (Table 3B).

3. Potent Antibacterial Effects of Novel Regimens Containing Repurposing Drugs.

As shown on Table 2A, antibacterial effects of thioridazine and chlorpromazine alone were potent in decreasing order on P.g., UA159, S.a. and P.a. Metformin alone was almost without this effect, but markedly increased by 20 to 80 fold in the novel regimens (Table 4). EGCG (E) appeared to be better than curcumin(C) and black tea polyphenols (T) in enhancing the antibacterial potencies on the 4 pathogens studied. Among them, E-MF-Zn was the best, E-TRZ-Zn and E-CPZ-Zn the next. The ruthenium red (RuR) containing regimens were also potent especially those on S.a. (Table 4). Further studies on the TRZ and CPZ regimens containing six metals ($Cu^{2+}$, $Ag^+$, $Mn^{2+}$, $VO_4^{2+}$, $Zn^{2+}$ and $Sr^{2+}$), showed their antibacterial effects were also potent but some of them marked with (X) were not as potent as they used alone (Table 5).

4. Antibacterial Effects of Novel Regimens Containing Membrane Transporter Blockers.

As shown on Table 2A, the membrane transporter blockers (verapamil, diltiazem, dithiothreitol, dibucaine and digitonin) alone were inactive, but their combinations exhibited potent antibacterial effects on P.g. and P.a. but not on UA159 and S.a. (Table 6).

5. Antibacterial Effects of Novel Regimens Containing Antibiotics and Polypeptides.

As shown on Table 3, antibiotics (tobramycin, rifampin and streptomycin) alone possessed very potent antibacterial effects but still exhibited more potent in some of the novel regimens (Table 7 and 8). The regimens containing polymycin B (PM) also appeared promising potent (Table 7). Although nystatin and isoniazid alone were almost inactive but became potent antibacterial in the novel regimens (Table 7). The polypeptides or toxin polypeptides combined with E-Q, E-F or E-R shown on Table 9 were extraordinarily potent in inhibiting the proliferation of P.g., UA159 and P.a. but not S.a. excepting that E-Q(F,R) RF were very potent in inhibiting S.a. On the other hand, the combinations of polypeptides with E-metals were less potent about 1/10 of the potency of the regimen as mentioned above containing E-Q, E-F or E-R (Tables 9 and 10).

6. Antibacterial Effects of Novel Regimens Containing Memantine, Metformin and Natural Products.

Although both memantine and metformin were almost inactive in antibacterial effects (Table 2A), they markedly synergistically exerted these effects in combination with various polyphenols-metallic compounds (Table 11). Similarly, the natural compounds (berberine, quercetin, tetramethylpyrazine and nordihydroguaiaretic acid) were by themselves very weak in antibacterial efficacy (Table 2B), but they markedly, synergistically exerted antibacterial effects in combination with polyphenolic-metallic compounds (Table 12).

7. Antibacterial Effects of Novel Regimens Containing Etidronate, Glibenclamide (Gbc) and 3,4-Diaminopyridine (3,4-DAP).

As shown on Table 13, the combinations of etidronate (Eti), glibenclamide (Gbc) and 3,4-diaminopyridine (3,4-DAP) with polyphenolic-metallic compounds also revealed promising antibacterial effects especially the regimen of C·Eti·metals were very potent in inhibiting proliferation of S.a. (Table 13A). Addition of memantine enhanced the antibacterial efficacy on P.g. of regimens containing Gbc or 3,4-DAP by about 2 fold (Table 13C).

8. Antibacterial Effects of Novel Regimens Containing Ag, Ge132 and Cisplatin (Pt).

As shown on Table 14, novel regimens containing Ag, Ge132 and cisplatin (Pt) exerted better antibacterial efficacy especially on P.a. and S.a.

9. Antibacterial Effects of the Mixtures of Herb Extracts

The mixtures of herb extracts (either GIM: the extract mixtures of Amla gooseberry, Rosehip fruit and yeast GSH; or OP, extract mixtures of bilberry, cassia seed, xangold and boxthorn combined with EGCG, licorice and peppermint oil, were found to be as potent as berberine and quercetin in their antibacterial effects (Table 15).

10. Selectivity of the Antibacterial Effects of the Novel Regimens Studied.

We have demonstrated that among the 282 effective antibacterial regimens tested, 83% of these effective regimens on the cultured pathogens were not inhibited on the proliferation of probiotic Lactobacillus reuteri (L.r.) even at the concentrations 3-10 times higher than $IC_{50}$ of each regimen respectively. Actually, some of these regimens especially those containing $MnCl_2$ markedly increased the L.r. growth (FIG. 1).

In FIG. 1, final concentrations (1×: mg/ml·mg/ml·mM) of drug combinations are as following:
NaF: 1 mg/ml
EQCu: 0.1·0.0003·0.03
EQMn: 0.1·0.0003·0.03
EFCu: 0.1·0.03·0.03
EFMn: 0.1·0.03·0.03
EFSr: 0.1·0.03·0.1

11. Selective Anticancer Effects of the Novel Regimens.

As shown on Table 16, the novel regimens containing $VO_4^{2-}$ and RuR exerted more potent inhibitory effects on the cultured oral squamous carcinoma cells (OECM-1) as compared with those on the gingival keratinocytes SG cell line.

12. Increased Osteogenic Activities of the Novel Regimens:

As shown on FIG. 2A-2E, the novel regimens containing EGCG with the targeting drugs either dequalinium(Q), NaF (F), 4-hexyl-resorcinal(R), Memantine(mem), glibenclamide(Gbc) or 3,4-diaminopyridine(3,4-DAP) and the metal ions($ZnCl_2$, $SrCl_2$ or Ge132) could alter cell proliferation, alkaline phosphatase (ALP) activities and ARS mineral contents of cultured MC3T3-E1 cells.

It appeared that E-Mem-Sr, E-Q-Sr, E-R-Zn, E-Gbc-Zn (or Ge) and E-3,4-DAP-Sr were potent in increasing alkaline phosphatase activities of the cultured MC3T3-E1 cells. On the other hand, E-Q-Mem, E-F-Sr, E-Eti-Zn, E-Gbc-Mem.Sr and E-3,4-DAP-Sr±Mem increased the ARS mineral contents of the cultured MC3T3-E1 cells.

FIG. 2A-2E. Novel regimens increased alkaline phosphatase(ALP) and the ARS mineral contents of the cultured preosteoblast MC3T3-E1 cells.

Final concentrations of each drug combinations at one fold (1×, mg/ml·mg/ml·mM) are as following:
EMemZn, EEtiZn: 0.1·0.1·0.1; EMemSr, EEtiSr: 0.1·0.1·0.3; EQ: 0.15·0.0005; ER: 0.15·0.0075 mg/ml; EQMem: 0.1·0.0003·0.1 mg/ml; ERMem: 0.1·0.005·0.1 mg/ml; EQZn: 0.03·0.0001·0.01; EQSr: 0.03·0.0001·0.03; EFZn: 0.03·0.01·0.01; EFSr: 0.03·0.01·0.03; ERZn: 0.1·0.005·0.03; EGbcZn: 0.1·0.00066·0.1; EGbcSr: 0.1·0.00066·0.3; EGbcGe: 0.1·0.00066·0.033; EGbcZn-Mem: 0.075·0.0005·0.075·0.075 mg/ml; EGbcGeMem: 0.075·0.0005·0.025·0.075 mg/ml; EGbcSrMem: 0.075·0.0005·0.225·0.075 mg/ml; E34DAPZn: 0.1·0.03·0.1; E34DAPSr: 0.1·0.03·0.3; E34DAPGe: 0.1·0.03·0.03; E34DAPZnMem: 0.075·0.025·0.075·0.075 mg/ml; E34DAPSrMem: 0.075·0.025·0.225·0.075 mg/ml; E34DAPGeMem: 0.075·0.025·0.025·0.075 mg/ml.

13. Decreased Osteoclastogenic Effects of the Novel Regimens:

As shown on FIG. 3A-3D, E-Eti-$SeO_3$($VO_4$) and E-Clo-$VO_4$(Zn,Sr) decreased tartrate-resistant acid phosphatase activities of the cultured preosteoblast RAW cells. Final concentrations (1×: mg/ml·mg/ml·mM) of each drug combinations are as following:
EEtiCu: 0.1·0.1·0.1
EEtiSe(Mn,VO4,Zn): 0.1·0.1·0.1
EEtiSr: 0.1·0.1·0.3
ECloCu: 0.1·0.3·0.1
ECloSe(Mn,VO4,Zn): 0.1·0.3·0.1
ECloSr: 0.1·0.3·0.3

Figure 4A:
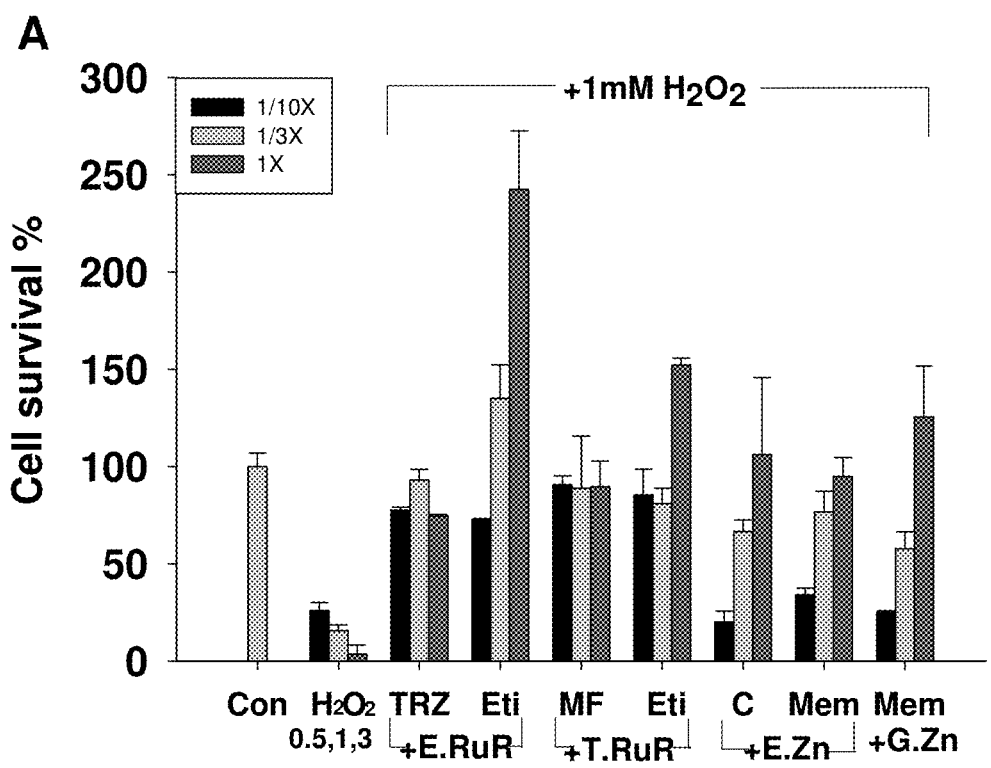
FIG. 4A shows the neuroprotective effects of novel regimens against $H_2O_2$-cytotoxicity in culture neuroblastoma cell.
Figure 4B:
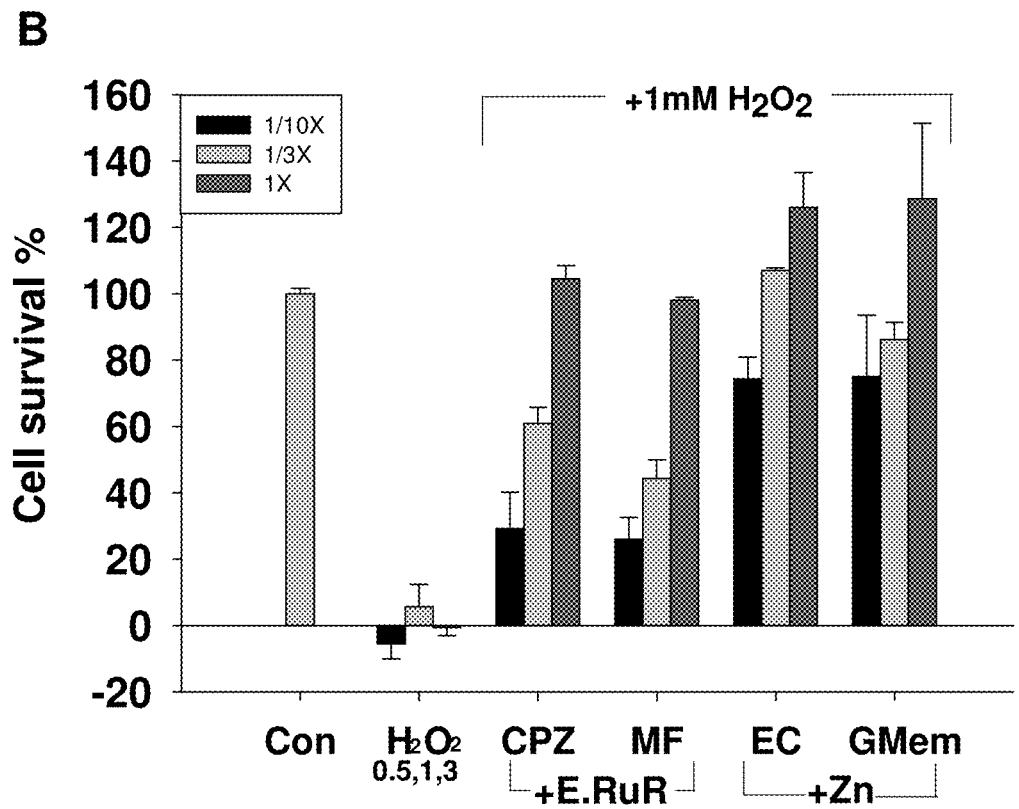
FIG. 4B shows the neuroprotective effects of novel regimens against $H_2O_2$-cytotoxicity in culture neuroblastoma cell.

14. Neuroprotective Effects of the Novel Regimens:

As shown on FIGS. 4A and 4B, the cytotoxic effects of $H_2O_2$ on cultured neuroblastoma SHSY5Y cells could be reduced by the regimens of E-TRZ(CPZ,MF)-RuR; T-MF (Eti)-RuR; E-C(Mem)-Zn and G-Mem-Zn respectively. The neuroprotective effects of the drugs are studied after 10 min (A) and 30 min (B) of H2O2 added to the cultured cell.

The concentration of H2O2 are 0.5, 1 and 3 mM respectively for the cytotoxicity test. Final concentrations of each drug combinations at one fold (1×, mg/ml·mg/ml·mM) are as following:
ETRZRuR, ECPZRuR: 0.3·0.03·0.035; EEtiRuR: 0.3·0.3·0.035; TMFRuR: 0.1·0.1·0.035;
TEtiRuR: 0.1·0.3·0.035; ECZn, EMemZn, GMemZn: 0.1·0.03·0.03; EMFRuR: 0.3·0.1·0.035.

Figure 5A:
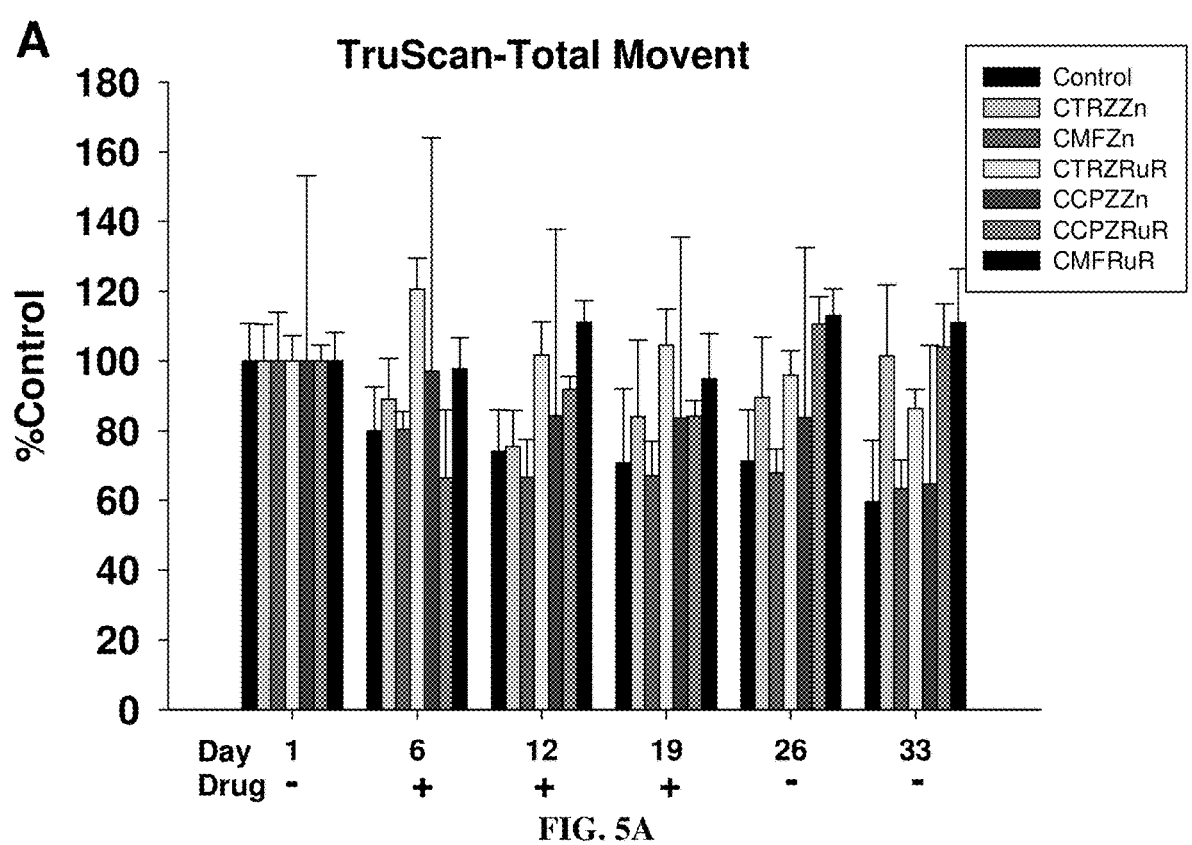
FIG. 5A shows the effects of the novel regimens on the locomotor activities of the mice after oral administrations of the drugs.
Figure 5B:
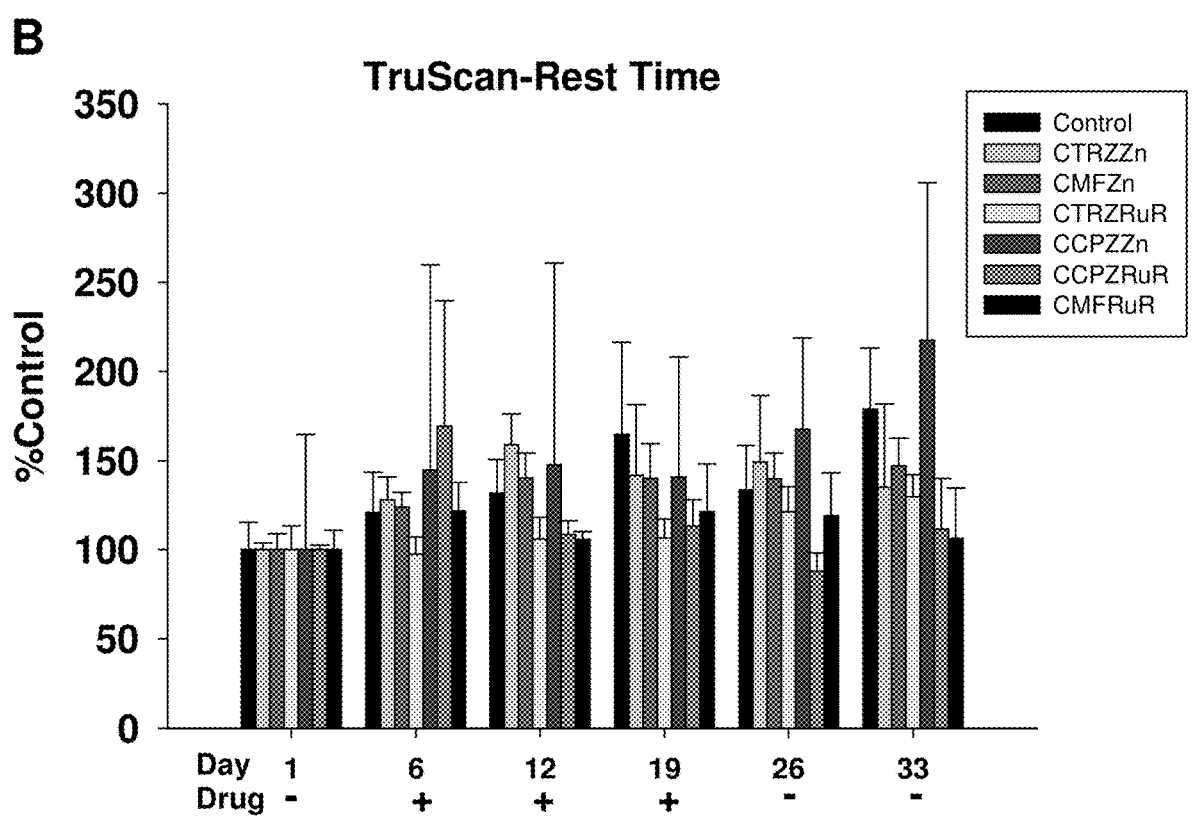
FIG. 5B shows the effects of the novel regimens on the locomotor activities of the mice after oral administrations of the drugs

15. Safety of Novel Regimens in Mice and Zebrafish:

The drug combinations (C-TRZ(CPZ,MF)-Zn(RuR) were orally administered to mice for 3 weeks showed safe and both C-TRZ(MF)-RuR slightly increased the locomotor activities (FIGS. 5A and 5B). Toxicity tests of regimens in zebrafish showed zero mortality after intramuscular injections for 1-5 days. In FIGS. 5A and 5B, final concentrations of each drug combinations at one fold (1×, mg/ml·mg/ml·mM) are as following:
CTRZZn, CCPZZn: 0.1·0.01·0.03; CTRZRuR, CCPZRuR: 0.1·0.01·0.035; CMFZn: 0.1·0.1·0.03; CMFRuR: 0.1·0.1·0.035.

Potential Applications of These Novel Regimens

1. Gut-Brain and oral cavity microbiomes have been extensively studied their relevance to human health and diseases (periodontitis, dementia, neurodegenerative diseases, diabetes, obesity, metabolic syndromes, inflammatory bowel disease, osteoporosis, cancers etc.). The novel regimens possessed not only anti-pathogenic effects but also enhanced the growth of probiotics, suggesting that they have a potential to alter the dysbiosis state to human homeostatic microbiome, leading to alleviate diseases and enhance healthy status.

2. Potential Applications in Management of Infections Diseases:

The various novel regimens showed pleiotropic inhibitory effects on the cultured pathogens. Recently, we cooperated with Drs. H. Y. Dou and T. L. Yang (Nat: Inst. Infectious Dis. And Vaccinology, Nat. Health Res. Institute (NHRI), Taiwan) to test the inhibitory effects of C-TRZ (CPZ, MF)-RuR on the multi-drug resistant (MDR) bacteria. A preliminary result showed that these novel regimens were effective in inhibiting the proliferation of MDR-*Mycobacterium tuberculosis*, MRSA and MDR-E falcalis.

3. Potential Applications in Neurodegenerative Diseases:

Our previous studies have shown that EGCG was synergistically with memantine for attenuating mouse CNS neuroexcitotoxicity.

The novel regimens of E(C,G)-Mem-Metals were proposed to exert both neuroprotection and modulation on oral microbiome (decreased periodontis) which may be benefial to managements of dementia, Parkinson's diseases and other neurogenerative disease. Similarly, E (T)-TRZ (CPZ,MF, Eti)-RuR exhibited neuroprotective effects against $H_2O_2$ oxidative cytotoxicity. Thus, they may have the potential benefit for prevention of these neurodegenerative diseases.

4. Prevention and Therapy of Metabolic Syndromes, Diabetes and Obesity.

The regimens containing metformin (E(C, G)-MF-Zn (RuR)) would be potentially more effective than metformin alone for prevention and treatment of these metabolic diseases.

5. For Prevention and Therapy of Osteoporosis.

The novel regimens containing etidronate, $Zn^{2+}$, $Sr^{2+}$, memantine, glibenclamide(Gbc) and 3,4-diaminopyridine revealed to be promising in increasing alkaline phosphatase (ALP) activities of the preosteoblast (MC3T3-E1) cells (FIG. 2A-2E), while E, Eti(Clo)VO4 and E, Clo, Zn(Sr) decreased tartrate resistant acid phosphatase(TRAP) activities of preosteoclast (RAW) cells (FIG. 3A-3D). These regimens may have potential application for prevention and therapy of osteoporosis.

6. For Prevention and Therapy of Cancers:

The selective anticancer effects of the novel regimen on the cultured oral cancer cells (OECM-1) as revealed in table 17 may have potential application in prevention and therapy of cancers.

7. For Prevention and Therapy of Chronic Pain:

We have previously reported that combinations of tea polyphenols and Memantine were effective not only in attenuating oralfacial pain but also suppressed morphine analgesic tolerance. The regimens of E(C, G)-Mem(MF)-Metals especially with RuR were expected to be effective in prevention and therapy of chronic pain.

Our experimental results (Tables 1 to 17) indicate that combination of tea polyphenol EGCG and memantine synergistically protected the brain against excitotoxicity (a cause of dementia, an American patent, Pub No.: US 2014/0094513). A series of different trial combinations (Tables 1, 2 and 3) containing EGCG (E), curcumin (C), green tea polyphenols (G), cinnamon (CC) or theaflavins (T), combined with memantine (Mem), metformin (MF), thioridazine (TRZ), chlorpromazine (CPZ), tobramycinrifampin, strepotomycin, isoniazide, verapamil, diltiazem, dithiothretol, dibucaine, cisplatin, dequalinium, 4-hexylresorcinol, ursodeoxycholic acid or etidronate (Eti) plus metal ion; either $Cu^{2+}$, $Mn^{2+}$, $Zn^{2+}$, $VO_4^{2+}$, $Sr^{2+}$, $SeO_3^{-2}$, $Ag^+$, Ge132 or ruthenium red (RuR) revealed a synergistic broad spectrum potent anti-microbial effects against *Porphyromonas gingivalis* (P.g.), *Streptococcus mutans* (UA159), *E. coli, Pseudomonas aeruginosa* (P.a.), *Bacillus subtilis* (B.s.), *Staphytococcus aureus* (S.a.) accompanied with anticancer effect (OECM-1). We believe that these novel regimens provide the safe therapeutic armamentarium to combat these incurable diseases.

The invention includes embodiments in which exactly one member of the group is present in, employed in, or otherwise relevant to a given product or process. The invention includes embodiments in which more than one, or all of the group members are present in, employed in, or otherwise relevant to a given product or process.

Those skilled in the art will recognize, or be able to ascertain by using no more than routine experimentation, many equivalents to the specific embodiments of the invention, described herein. The scope of the present invention is not intended to be limited to the particular embodiments disclosed, but rather includes all embodiments falling within the scope of the appended claim. In addition, many modifications will be appreciated to adapt a particular instrument, situation or material to the teachings of the invention without departing from the essential scope thereof.

REFERENCES

1. Franceschi, Claudio, et al. "The Continuum of Aging and Age-Related Diseases: Common Mechanisms but Different Rates." *Frontiers in medicine* 5 (2018): 61.
2. Zhang, Tianlang, et al. "Comparative Epidemiological Investigation of Alzheimer's Disease and Colorectal Cancer: The Possible Role of Gastrointestinal Conditions in the Pathogenesis of AD." *Frontiers in aging neuroscience* 10 (2018).

3. Tzeng, Nian-Sheng, et al. "Are chronic periodontitis and gingivitis associated with dementia? A nationwide, retrospective, matched-cohort study in Taiwan." *Neuroepidemiology* 47.2 (2016): 82-93.
4. Chen, Chang-Kai, Yung-Tsan Wu, and Yu-Chao Chang. "Association between chronic periodontitis and the risk of Alzheimer's disease: a retrospective, population-based, matched-cohort study." *Alzheimer's research & therapy* 9.1 (2017): 56.
5. Spielman, Lindsay Joy, Deanna Lynn Gibson, and Andis Klegeris. "Unhealthy gut, unhealthy brain: The role of the intestinal microbiota in neurodegenerative diseases." *Neurochemistry international* (2018).
6. Rybnikova, Elena. "Brain, antibiotics, and microbiota—how do they interplay? An Editorial for 'Antibiotics-induced modulation of large intestinal microbiota altered aromatic amino acid profile and expression of neurotransmitters in the hypothalamus of piglets' on page 219." *Journal of neurochemistry* 146.3 (2018): 208-210.
7. Giau, Vo, et al. "Gut Microbiota and Their Neuroinflammatory Implications in Alzheimer's Disease." *Nutrients* 10.11 (2018): 1765.
8. Junges, Vilma M., et al. "Crosstalk between Gut Microbiota and Central Nervous System: A Focus on Alzheimer's Disease." *Current Alzheimer Research* 15.13 (2018): 1179-1190.
9. Sochocka, Marta, et al. "The Gut Microbiome Alterations and Inflammation-Driven Pathogenesis of Alzheimer's Disease—a Critical Review," *Molecular Neurobiology:* 1-11.
10. Pritchard, Anna B., et al. "Periodontitis, microbiomes and their role in Alzheimer's disease." *Frontiers in Aging Neuroscience* 9 (2017): 336.
11. Solas, Maite, et al. "Inflammation and gut-brain axis link obesity to cognitive dysfunction: plausible pharmacological interventions." *Current opinion in pharmacology* 37 (2017): 87-92.
12. Ide, Mark, et al. "Periodontitis and cognitive decline in Alzheimer's disease." *PLoS One* 11.3 (2016): e0151081.
13. Lin, Yu-Li, et al. "Composition of polyphenols in fresh tea leaves and associations of their oxygen-radical-absorbing capacity with antiproliferative actions in fibroblast cells." *Journal of Agricultural and Food Chemistry* 44.6 (1996): 1387-1394.
14. Lin, Jen-Kun, "Cancer chemoprevention by tea polyphenols through modulating signal transduction pathways." *Archives of pharmacal research* 25.5 (2002): 561.
15. Lin, Jen-Kun, and Shoei-Yn Lin-Shiau. "Mechanisms of hypolipidemic and anti-obesity effects of tea and tea polyphenols." *Molecular nutrition & food research* 50.2 (2006): 211-217.
16. Deng, Yea-Tzy, and Jen-Kun Lin, "EGCG inhibits the invasion of highly invasive CL1-5 lung cancer cells through suppressing MMP-2 expression via JNK signaling and induces G2/M arrest." *Journal of agricultural and food chemistry* 59.24 (2011): 13318-13327.
17. Huang, Hsiu-Chen, and Jen-Kun Lin. "Pu-erh tea, green tea, and black tea suppresses hyperlipidemia, hyperleptinemia and fatty acid synthase through activating AMPK in rats fed a high-fructose diet." *Food & function* 3.2 (2012): 170-177.
18. Yang, Tsung-Yuan, et al. "Weight reduction effect of Puerh tea in male patients with metabolic syndrome." *Phytotherapy research* 28.7 (2014): 1096-1101.
19. Chen S H, Lin J K, Liang Y C, Pan M H, Liu S H, Lin-Shiau S Y. "Involvement of activating transcription factors JNK, NF-kappaB, and AP-1 in apoptosis induced by pyrrolidine dithiocarbamate/Cu complex" *Eur J Pharmacol* (2008): 9-17.
20. Chen S H, Lin J K, Liu S H, Liang Y C, Lin-Shiau S Y. "Apoptosis of cultured astrocytes induced by the copper and neocuproine complex through oxidative stress and JNK activation." *Toxicol Sci*. (2008): 138-149
21. Cheng P W, Liu S H, Hsu C J, Lin-Shiau S Y. "Correlation of increased activities of Na+, K+-ATPase and Ca2+-ATPase with the reversal of cisplatin ototoxicity induced by D-methionine in guinea pigs." *Hear Res*. (2005): 102-109
22. Hsu C J, Chen Y S, Shau W Y, Yeh T H, Lee S Y, Lin-Shiau S Y. "Impact of activities of Na(+)-K(+)-ATPase and Ca2(+)-ATPase in the cochlear lateral wall on recovery from noise-induced temporary threshold shift." *Ann Otol Rhinol Laryngol*. (2002): 842-849
23. Chang-Mu C, Jen-Kun L, Shing-Hwa L, Shoei-Yn L S. "Characterization of neurotoxic effects of NMDA and the novel neuroprotection by phytopolyphenols in mice." *Behav Neurosci*. (2010): 541-553
24. Chen C M, Lin J K, Liu S H, Lin-Shiau S Y. "Novel regimen through combination of memantine and tea polyphenol for neuroprotection against brain excitotoxicity." *J Neurosci Res*. (2008): 2696-2704
25. Chen C M, Liu S H, Lin-Shiau S Y. "Honokiol, a neuroprotectant against mouse cerebral ischaemia, mediated by preserving Na+, K+-ATPase activity and mitochondrial functions." *Basic Clin Pharmacol Toxicol*. (2007): 108-116
26. Lin Shiau, Shoei Yn and Kao, Chia Tze. "Tea Polyphenols Synergistic Enhancement of Antibacterial Effects of NaF on the Cultured *Streptococcus Mutans.*" *Biomed J Sci & Tech Res* (2018).
27. Worton L E, Shi Y C, Smith E J, Barry S C, Gonda T J, Whitehead J P, Gardiner E M. "Ectodermal-Neural Cortex 1 Isoforms Have Contrasting Effects on MC3T3-E1 Osteoblast Mineralization and Gene Expression." *J Cell Biochem*. (2017): 2141-2150
28. Park J K, Rosen A, Saffitz J E, Asimaki A, Litovsky S H, Mackey-Bojack S M, Halushka M K."
   Expression of cathepsin K and tartrate-resistant acid phosphatase is not confined to osteoclasts but is a general feature of multinucleated giant cells: systematic analysis." *Rheumatology (Oxford)*. (2013): 1529-1533
29. Tseng W P, Lin-Shiau S Y. "Activation of NMDA receptor partly involved in beta-bungarotoxin-induced neurotoxicity in cultured primary neurons." *Neurochem Int*. (2003): 333-344
30. Tseng W P, Lin-Shiau S Y. "Long-term lithium treatment prevents neurotoxic effects of beta-bungarotoxin in primary cultured neurons." *J Neurosci Res*. (2002): 633-641
31. Chuu J J, Huang Z N, Yu H H, Chang L H, Lin-Shiau S Y. "Attenuation by methyl mercury and mercuric sulfide of pentobarbital induced hypnotic tolerance in mice through inhibition of ATPase activities and nitric oxide production in cerebral cortex." *Arch Toxicol*. (2008): 343-353
32. Huang C F, Liu S H, Lin-Shiau S Y. "Neurotoxicological effects of cinnabar (a Chinese mineral medicine, HgS) in mice." *Toxicol Appl Pharmacol*. (2007): 192-201
33. Chou T C. "Drug comination studies and their synergy quantification using the Chou-Talalay Method." *Cancer research*. (2010): 440-446

TABLE 1

Concentrations of polyphenols, metalions and polyphenol-metal combimetal salts for 50% inhibitions on antibacterial effects ($IC_{50}$).

A.

| Polyphenols | $IC_{50}$ (mg/ml) | | | |
|---|---|---|---|---|
| | P. g. | UA159 | P. a. | S. a. |
| E, EGCG | 0.083 | 0.137 | 0.173 | 0.142 |
| G, Green tea polyphenols | 0.044 | 0.135 | 0.180 | 0.384 |
| T*, Black tea polyphenols | 0.167 | 0.124 | 0.291 | 0.150 |
| C*, Curcumin | 0.126 | 0.042 | 0.302 | <1 |
| CC, cinnamon | >0.3 | >0.3 | >0.3 | >0.3 |

B.

| Metals | $IC_{50}$ (mM) | | | |
|---|---|---|---|---|
| | P. g. | UA159 | P. a. | S. a. |
| $CuCl_2$ | 0.673 | 0.448 | 1.691 | >2 |
| AgCl* | 0.014 | 0.035 | 0.044 | 0.028 |
| $MnCl_2$* | 0.990 | 1.435 | >2 | 2.742 |
| $Na_3VO_4$ | 0.217 | 0.866 | >2 | >2 |
| $ZnSO_4$* | 1.063 | 0.961 | 1.159 | 0.939 |
| $SrCl_2$* | >3 | >3 | 4.193 | 3.593 |
| RuR*, Ruthenium red | 0.074 | 0.644 | 0.032 | >0.116 |

C.

| Drugs | $IC_{50}$ (mg/ml · mM) | | | |
|---|---|---|---|---|
| | P. g. | UA159 | P. a. | S. a. |
| E · Cu* | 0.113 · 0.013 | 0.113 · 0.013 | 0.092 · 0.010 | 0.091 · 0.010 |
| E · Ag* | 0.122 · 0.014 | 0.134 · 0.004 | 0.096 · 0.003 | 0.122 · 0.004 |
| E · Mn* | 0.095 · 0.011 | 0.141 · 0.016 | 0.090 · 0.010 | 0.117 · 0.013 |
| E · $VO_4$* | 0.081 · 0.009 | 0.143 · 0.16 | 0.084 · 0.009 | 0.175 · 0.019 |
| E · Zn* | 0.066 · 0.007 | 0.098 · 0.011 | 0.085 · 0.009 | 0.121 · 0.013 |
| E · Sr* | 0.076 · 0.025 | 0.098 · 0.033 | 0.084 · 0.028 | 0.127 · 0.042 |
| E · RuR* | 0.052 · 0.020 | 0.057 · 0.022 | 0.032 · 0.013 | 0.059 · 0.023 |
| C · Cu | 0.032 · 0.011 | 0.036 · 0.012 | 0.111 · 0.037 | 0.053 · 0.018 |
| C · Ag* | 0.107 · 0.011 | >0.15 · 0.015 | >0.15 · 0.015 | >0.15 · 0.015 |
| C · Mn* | >0.15 · 0.05 | >0.15 · 0.05 | >0.15 · 0.05 | >0.15 · 0.05 |
| C · $VO_4$ | 0.066 · 0.022 | 0.048 · 0.016 | 0.088 · 0.029 | 0.046 · 0.015 |
| C · Zn* | >0.15 · 0.05 | >0.15 · 0.05 | >0.15 · 0.05 | >0.15 · 0.05 |
| C · Sr* | >0.15 · 0.15 | >0.15 · 0.15 | >0.15 · 0.15 | >0.15 · 0.15 |
| C · RuR | 0.105 · 0.041 | 0.049 · 0.019 | 0.043 · 0.016 | 0.051 · 0.020 |
| G · Cu* | 0.039 · 0.006 | 0.107 · 0.018 | 0.340 · 0.057 | >0.3 · 0.05 |
| G · Ag* | 0.017 · 0.001 | 0.101 · 0.005 | 0.131 · 0.007 | >0.3 · 0.015 |
| G · Mn* | 0.025 · 0.004 | 0.112 · 0.019 | 0.126 · 0.021 | >0.3 · 0.05 |
| G · $VO_4$* | 0.052 · 0.009 | 0.436 · 0.073 | >0.3 · 0.05 | >0.3 · 0.05 |
| G · Zn* | 0.022 · 0.004 | 0.112 · 0.019 | 0.146 · 0.024 | >0.3 · 0.05 |
| G · Sr* | 0.027 · 0.013 | 0.101 · 0.051 | 0.139 · 0.069 | >0.3 · 0.15 |
| G · RuR* | 0.021 · 0.013 | >0.15 · 0.058 | 0.039 · 0.022 | >0.15 · 0.058 |
| T · Cu* | 0.111 · 0.037 | 0.072 · 0.024 | >0.15 · 0.05 | >0.15 · 0.05 |
| T · Ag* | 0.048 · 0.005 | 0.194 · 0.019 | >0.15 · 0.015 | >0.15 · 0.015 |
| T · Mn* | 0.099 · 0.033 | >0.15 · 0.05 | >0.15 · 0.05 | >0.15 · 0.05 |
| T · $VO_4$* | 0.032 · 0.011 | >0.15 · 0.05 | >0.15 · 0.05 | >0.15 · 0.05 |
| T · Zn* | 0.045 · 0.015 | >0.15 · 0.05 | 0.149 · 0.050 | >0.15 · 0.05 |
| T · Sr* | 0.070 · 0.070 | 0.121 · 0.121 | >0.15 · 0.15 | >0.15 · 0.15 |
| T · RuR* | 0.124 · 0.048 | 0.029 · 0.012 | 0.053 · 0.021 | >0.15 · 0.058 |
| CC · Cu* | >0.15 · 0.05 | >0.15 · 0.05 | >0.15 · 0.05 | >0.15 · 0.05 |
| CC · Ag* | >0.15 · 0.015 | >0.15 · 0.015 | >0.15 · 0.015 | >0.15 · 0.015 |
| CC · Mn* | >0.15 · 0.05 | >0.15 · 0.05 | >0.15 · 0.05 | >0.15 · 0.05 |

TABLE 1-continued

Concentrations of polyphenols, metalions and polyphenol-metal combimetal salts for 50% inhibitions on antibacterial effects ($IC_{50}$).

| | | | | |
|---|---|---|---|---|
| CC · $VO_4$* | >0.15 · 0.05 | >0.15 · 0.05 | >0.15 · 0.05 | >0.15 · 0.05 |
| CC · Zn* | >0.15 · 0.05 | >0.15 · 0.05 | >0.15 · 0.05 | >0.15 · 0.05 |
| CC · Sr* | >0.15 · 0.15 | >0.15 · 0.15 | >0.15 · 0.15 | >0.15 · 0.15 |
| CC · RuR* | 0.049 · 0.028 | >0.15 · 0.058 | 0.042 · 0.024 | >0.15 · 0.058 |

P. g., Porphyromobas gingivalis;
UA159, Streptococcus mutans;
P. a., Pseudomonas aeruphosa;
S. a., Staphylococcus aureus.
$IC_{50}$, concentrations of 50% inhibition on bacterial proliferation.
*The drug combinations listed in this table at concentrations of 3 to 10 times higher than the listed $IC_{50}$ have no inhibition on the proliferation of the cultured Lactobacillus reuteti

TABLE 2

Concentrations of repurposing drugs (A) and natural products (B) for 50% inhibitions on bacterial proliferation ($IC_{50}$).

| | $IC_{50}$ (mg/ml) | | | |
|---|---|---|---|---|
| Drugs | P. g. | UA159 | P. a. | S. a. |
| A. | | | | |
| DQ, Dequalinium | 0.003 | 0.001 | >0.01 | 0.002 |
| F, NaF | 0.666 | 0.01 | | |
| R, 4-Hexyl-Resorcinol | 0.020 | 0.015 | >0.1 | 0.032 |
| Mem, Memantine | 0.059 | 0.386 | 0.321 | 0.435 |
| MF, Metformin* | 0.639 | >1 | >1 | >1 |
| TRZ, Thioridazine* | 0.006 | 0.012 | 0.104 | 0.013 |
| CPZ, Chlorpromazine* | 0.005 | 0.007 | 0.149 | 0.012 |
| Eti, Etidronate | 0.046 | 0.597 | >1 | 0.350 |
| Qn, Quinine | 0.043 | >0.1 | >0.1 | >0.1 |
| VP, Verapamil | 0.137 | >0.3 | >0.3 | >0.3 |
| Di, Diltiagem | 0.104 | >0.3 | >0.3 | >0.3 |
| DT, Dithiothreitol | >0.3 | >0.3 | >0.3 | >0.3 |
| DG, Digitonin | 0.123 | >0.3 | >0.3 | >0.3 |
| B. | | | | |
| Bb, Berberine | >0.1 | 0.025 | >0.1 | >0.1 |
| Lz, Lysozyme | 0.021 | >0.1 | >0.1 | >0.1 |
| Qc, Quercetin | >0.1 | 0.046 | >0.1 | >0.1 |
| TMP, Tetramethyl-pyrazine | 0.037 | >0.3 | >0.3 | >0.3 |
| NDGA, Nordihydro-guaiaretic acid | <0.03 | 0.050 | >0.3 | 0.066 |

P. g., Porphyromonas gingivalis;
UA159, Streptococcus mutans;
P. a., Pseudomonas aeruginosa;
S. a., Staphylococcus aureus.
$IC_{50}$, concentrations of 50% inhibition on bacterial proliferation.
* The drug combinations listed in this table at concentrations of 3 to 10 times higher $IC_{50}$ have no inhibition on the proliferation of the cultured Lactobacillus reuteri

TABLE 3

Concentrations of antibiotics (A) and polypeptides (B) for 50% inhibitions on bacterial proliferation ($IC_{50}$).

| | $IC_{50}$ (mg/ml) | | | |
|---|---|---|---|---|
| | P. g. | UA159 | P.a. | S. a. |
| A. | | | | |
| Antibiotics | | | | |
| Tb, Tobramycin | 0.004 | <0.003 | 0.009 | <0.003 |
| Ny, Nystatin | 0.228 | >0.3 | >0.3 | >0.3 |
| INH, Isoniazid | >0.3 | >0.3 | >0.3 | >0.3 |
| Rf, Rifampin | $4.5 \times 10^{-4}$ | $0.13 \times 10^{-4}$ | 0.026 | $0.13 \times 10^{-4}$ |
| St, Streptomycin | 0.009 | 0.021 | 0.005 | $2 \times 10^{-4}$ |
| B. | | | | |
| Polypeptides | | | | |
| PR, polyarginine | 0.025 | >0.1 | >0.1 | >0.1 |
| Pro, protamine | 0.031 | >0.1 | >0.1 | >0.1 |
| PK37, polylysine37 | 0.086 | >0.1 | >0.1 | >0.1 |
| PK84, polylysine84 | 0.050 | >0.1 | >0.1 | >0.1 |
| RF, ArgPhe | >0.1 | >0.1 | >0.1 | >0.1 |
| NTX, Notexin | >0.01 | >0.01 | >0.01 | >0.01 |
| CTX14, Cardiotoxin | 0.011 | >0.01 | >0.01 | >0.01 |
| PLA2, Phospholipase $A_2$ | >0.01 | >0.01 | >0.01 | >0.01 |
| α-BuTx, α-Bungarotoxin | >0.01 | >0.01 | >0.01 | >0.01 |
| β-BuTx, β-Bungarotoxin | >0.03 | >0.03 | >0.03 | >0.03 |

P. g., Porphyromonas gingivalis;
UA159, Streptococcus mutans;
P. a., Pseudomonas aeruginosa;
S. a., Staphylococcus aureus
$IC_{50}$, concentrations of 50% inhibition on bacterial proliferation.

TABLE 4

Antibacterial effects of norvel regimens of repurposing drugs.

| Drugs | IC$_{50}$ (mg/ml · mg/ml · mM) | | | |
|---|---|---|---|---|
| | P. g. | UA159 | P. a. | S. a. |
| E · TRZ · Zn* | 0.01 · 0.0003 · 0.001 | 0.130 · 0.004 · 0.013 | 0.066 · 0.002 · 0.007 | 0.159 · 0.005 · 0.016 |
| E · CPZ · Zn* | 0.021 · 0.001 · 0.002 | 0.161 · 0.005 · 0.016 | 0.062 · 0.002 · 0.006 | 0.168 · 0.006 · 0.017 |
| E · MF · Zn | 0.012 · 0.004 · 0.001 | 0.111 · 0.037 · 0.011 | 0.061 · 0.020 · 0.006 | 0.153 · 0.051 · 0.015 |
| E · TRZ · RuR | 0.024 · 0.001 · 0.002 | 0.114 · 0.004 · 0.013 | 0.047 · 0.002 · 0.006 | 0.143 · 0.005 · 0.016 |
| E · CPZ · RuR | 0.015 · 0.001 · 0.001 | 0.082 · 0.003 · 0.009 | 0.021 · 0.002 · 0.006 | 0.136 · 0.005 · 0.016 |
| E · MF · RuR | 0.028 · 0.009 · 0.003 | 0.109 · 0.036 · 0.013 | 0.044 · 0.015 · 0.005 | 0.132 · 0.044 · 0.015 |
| C · TRZ · Zn* | 0.034 · 0.003 · 0.010 | 0.021 · 0.002 · 0.006 | >0.1 · 0.01 · 0.03 | >0.1 · 0.01 · 0.03 |
| C · CPZ · Zn* | 0.026 · 0.003 · 0.008 | 0.021 · 0.002 · 0.006 | >0.1 · 0.01 · 0.03 | >0.1 · 0.01 · 0.03 |
| C · MF · Zn | 0.032 · 0.032 · 0.009 | 0.027 · 0.027 · 0.008 | >0.1 · 0.1 · 0.03 | >0.1 · 0.1 · 0.03 |
| C · TRZ · RuR | 0.021 · 0.002 · 0.007 | 0.027 · 0.003 · 0.009 | 0.030 · 0.003 · 0.010 | 0.038 · 0.004 · 0.013 |
| C · CPZ · RuR | 0.019 · 0.002 · 0.007 | 0.023 · 0.002 · 0.008 | 0.031 · 0.003 · 0.010 | 0.041 · 0.004 · 0.014 |
| C · MF · RuR | 0.023 · 0.023 · 0.008 | 0.022 · 0.022 · 0.008 | 0.040 · 0.040 · 0.014 | 0.039 · 0.039 · 0.014 |
| T · TRZ · RuR* | 0.038 · 0.012 · 0.014 | 0.037 · 0.011 · 0.013 | 0.036 · 0.011 · 0.013 | >0.1 · 0.03 · 0.035 |
| T · Mem3 · RuR* | 0.040 · 0.040 · 0.014 | 0.045 · 0.045 · 0.015 | 0.035 · 0.035 · 0.012 | >0.1 · 0.1 · 0.035 |
| T · MF · RuR* | 0.040 · 0.040 · 0.014 | 0.135 · 0.135 · 0.048 | 0.035 · 0.035 · 0.012 | >0.1 · 0.1 · 0.035 |
| T · CPZ · RuR* | 0.027 · 0.008 · 0.009 | 0.033 · 0.010 · 0.012 | 0.034 · 0.010 · 0.012 | >0.1 · 0.03 · 0.035 |
| T · Mem1 · RuR* | 0.038 · 0.012 · 0.014 | 0.049 · 0.015 · 0.017 | 0.039 · 0.012 · 0.014 | >0.1 · 0.03 · 0.035 |
| T · Eti · RuR* | 0.029 · 0.088 · 0.010 | 0.270 · 0.881 · 0.094 | 0.026 · 0.077 · 0.009 | >0.1 · 0.3 · 0.035 |

P. g., Porphyromonas gingivalis;
UA159, Streptococcus mutans;
P. a., Pseudomonas aeruginosa;
S. a., Staphylococcus aureus
IC50, concentrations of 50% inhibition on bacterial proliferation.
*The drug combinations listed in this table at concentrations of 3 to 10 times higher than the listed IC$_{50}$ have no inhibition on the proliferation of the cultured Lactobacillus reuteri.

TABLE 5

Antibacterial effects of thioridazine (TRZ) and chlopromazine (CPZ) regimens.

| Drugs | IC$_{50}$ (mg/ml · mg/ml · mM) | | | |
|---|---|---|---|---|
| | P. g. | UA159 | P. a. | S. a. |
| E · TRZ · Cu* | 0.052 · 0.005 · 0.015 | 0.029 · 0.003 · 0.009 | 0.183 · 0.018 · 0.055 | 0.048 · 0.005 · 0.014 |
| E · TRZ · Ag* | 0.056 · 0.006 · 0.006 | 0.024 · 0.002 · 0.002 | 0.088 · 0.008 · 0.008 | 0.043 · 0.004 · 0.004 |
| E · TRZ · Mn* | 0.084 · 0.008 · 0.025 | 0.069 · 0.007 · 0.021 | 0.132 · 0.013 · 0.039 | 0.041 · 0.004 · 0.012 |
| E · TRZ · VO$_4$* | 0.018 · 0.002 · 0.005 | >0.1 · 0.01 · 0.03 | >0.1 · 0.01 · 0.03 | 0.194 · 0.019 · 0.058 |
| E · TRZ · Zn* | 0.043 · 0.004 · 0.013 | 0.052 · 0.005 · 0.016 | 0.662 · 0.066 · 0.199 | 0.076 · 0.008 · 0.023 |
| E · TRZ · Sr* | >0.1 · 0.01 · 0.1 | 0.056 · 0.006 · 0.056 | 0.098 · 0.010 · 0.098 | 0.060 · 0.006 · 0.060 |
| C · TRZ · Cu* | 0.042 · 0.004 · 0.013 | 0.130 · 0.013 · 0.039 | 0.151 · 0.015 · 0.045 | 0.028 · 0.003 · 0.008 |
| C · TRZ · Ag* | 0.032 · 0.003 · 0.003 | 0.084 · 0.008 · 0.008 | 0.066 · 0.007 · 0.007 | 0.025 · 0.003 · 0.003 |
| C · TRZ · Mn* | 0.030 · 0.003 · 0.009 | 0.052 · 0.005 · 0.016 | 0.240 · 0.024 · 0.072 | 0.074 · 0.007 · 0.022 |
| C · TRZ · VO$_4$ | 0.018 · 0.002 · 0.005 | 0.147 · 0.015 · 0.044 | 0.226 · 0.023 · 0.068 | 0.031 · 0.003 · 0.009 |
| C · TRZ · Zn* | 0.019 · 0.002 · 0.006 | >0.1 · 0.01 · 0.03 | 0.109 · 0.011 · 0.033 | 0.024 · 0.002 · 0.007 |
| C · TRZ · Sr* | 0.016 · 0.002 · 0.016 | 0.626 · 0.063 · 0.626 | 0.171 · 0.017 · 0.171 | 0.030 · 0.003 · 0.030 |
| E · CPZ · Cu | 0.023 · 0.007 · 0.023 | 0.024 · 0.007 · 0.024 | | 0.080 · 0.024 · 0.080 |
| E · CPZ · Ag | 0.015 · 0.005 · 0.010 | 0.026 · 0.008 · 0.017 | | 0.053 · 0.016 · 0.053 |
| E · CPZ · Mn | 0.019 · 0.006 · 0.019 | 0.191 · 0.057 · 0.191 | | 0.046 · 0.014 · 0.046 |
| E · CPZ · VO$_4$ | 0.023 · 0.007 · 0.023 | 0.135 · 0.040 · 0.135 | | >0.1 · 0.03 · 0.1 |
| E · CPZ · Zn* | 0.029 · 0.009 · 0.029 | 0.036 · 0.011 · 0.036 | | 0.046 · 0.014 · 0.046 |
| E · CPZ · Sr | 0.025 · 0.008 · 0.076 | 0.034 · 0.010 · 0.101 | | 0.039 · 0.012 · 0.116 |
| C · CPZ · Cu | 0.089 · 0.009 · 0.027 | 0.009 · 0.009 · 0.030 | 0.126 · 0.013 · 0.038 | 0.078 · 0.008 · 0.023 |
| C · CPZ · Ag | 0.038 · 0.004 · 0.004 | 0.011 · 0.011 · 0.025 | 0.063 · 0.006 · 0.006 | 0.071 · 0.007 · 0.007 |
| C · CPZ · Mn* | 0.078 · 0.008 · 0.023 | 0.011 · 0.011 · 0.036 | 0.082 · 0.008 · 0.025 | 0.045 · 0.004 · 0.013 |
| C · CPZ · VO$_4$ | 0.125 · 0.013 · 0.038 | >0.03 · 0.03 · 0.1 | 0.086 · 0.009 · 0.026 | 0.042 · 0.004 · 0.013 |
| C · CPZ · Zn* | 0.110 · 0.011 · 0.033 | 0.011 · 0.011 · 0.037 | 0.048 · 0.005 · 0.015 | 0.038 · 0.004 · 0.011 |
| C · CPZ · Sr* | 0.097 · 0.010 · 0.097 | 0.010 · 0.010 · 0.103 | 0.057 · 0.006 · 0.057 | 0.046 · 0.005 · 0.046 |

P. g., Porphyromonas gingivalis;
UA159, Streptococcus mutans;
P. a., Pseudomonas aeruginosa;
S. a., Staphylococcus aureus
IC$_{50}$, concentrations of 50% inhibition on bacterial proliferation.
*The drug combinations listed in this table at concentrations of 3 to 10 times higher than the listed IC$_{50}$ have no inhibition on the proliferation of the cultured Lactobacillus reuteri.

TABLE 6

Antibacterial effects of novel regimens containing membrane transporter blockers.

| | $IC_{50}$ (mg/ml · mg/ml · mg/ml) | | | |
|---|---|---|---|---|
| Drugs | P. g. | UA159 | P. a. | S. a. |
| E · VP · Cu** | 0.021 · 0.006 · 0.006 | 0.094 · 0.028 · 0.028 | 0.062 · 0.019 · 0.019 | >0.1 · 0.03 · 0.03 |
| E · VP · Mn | 0.019 · 0.006 · 0.006 | 0.050 · 0.015 · 0.015 | 0.054 · 0.016 · 0.016 | >0.1 · 0.03 · 0.03 |
| E · VP · Zn | 0.014 · 0.004 · 0.004 | >0.1 · 0.03 · 0.03 | 0.054 · 0.016 · 0.016 | >0.1 · 0.03 · 0.03 |
| C · VP · Cu | 0.060 · 0.018 · 0.018 | >0.1 · 0.03 · 0.03 | 0.059 · 0.018 · 0.018 | >0.1 · 0.03 · 0.03 |
| C · VP · Mn | 0.040 · 0.012 · 0.012 | >0.1 · 0.03 · 0.03 | >0.1 · 0.03 · 0.03 | >0.1 · 0.03 · 0.03 |
| C · VP · Zn | 0.040 · 0.012 · 0.012 | >0.1 · 0.03 · 0.03 | >0.1 · 0.03 · 0.03 | >0.1 · 0.03 · 0.03 |
| E · Q · VP | 0.013 · 0.00004 · 0.004 | >0.1 · 0.0003 · 0.03 | 0.042 · 0.0001 · 0.013 | >0.1 · 0.0003 · 0.03 |
| E · F · VP | 0.01 · 0.004 · 0.004 | >0.1 · 0.03 · 0.03 | 0.04 · 0.013 · 0.013 | >0.1 · 0.03 · 0.03 |
| E · R · VP | 0.013 · 0.001 · 0.004 | 0.075 · 0.004 · 0.022 | 0.041 · 0.002 · 0.012 | >0.1 · 0.005 · 0.03 |
| E · Q · Di | 0.011 · 0.00003 · 0.003 | >0.1 · 0.0003 · 0.03 | 0.047 · 0.0001 · 0.014 | >0.1 · 0.0003 · 0.03 |
| E · F · Di | 0.01 · 0.003 · 0.003 | >0.1 · 0.03 · 0.03 | 0.05 · 0.016 · 0.016 | >0.1 · 0.03 · 0.03 |
| E · R · Di | 0.008 · 0.0004 · 0.002 | 0.089 · 0.004 · 0.027 | 0.047 · 0.002 · 0.014 | >0.1 · 0.005 · 0.03 |
| E · Q · DT | 0.026 · 0.0001 · 0.008 | >0.1 · 0.0003 · 0.03 | 0.087 · 0.0003 · 0.026 | >0.1 · 0.0003 · 0.03 |
| E · F · DT | 0.03 · 0.009 · 0.009 | >0.1 · 0.03 · 0.03 | 0.087 · 0.026 · 0.026 | >0.1 · 0.03 · 0.03 |
| E · R · DT | 0.021 · 0.001 · 0.006 | 0.045 · 0.002 · 0.013 | 0.077 · 0.004 · 0.023 | >0.1 · 0.005 · 0.03 |
| E · Q · DB | 0.025 · 0.0001 · 0.008 | >0.1 · 0.0003 · 0.03 | 0.076 · 0.0002 · 0.023 | >0.1 · 0.0003 · 0.03 |
| E · F · DB | 0.023 · 0.007 · 0.007 | >0.1 · 0.03 · 0.03 | 0.078 · 0.023 · 0.023 | >0.1 · 0.03 · 0.03 |
| E · R · DB | 0.019 · 0.001 · 0.006 | 0.041 · 0.002 · 0.012 | 0.085 · 0.004 · 0.025 | >0.1 · 0.005 · 0.03 |
| E · Q · DG | 0.016 · 0.00005 · 0.005 | >0.1 · 0.0003 · 0.03 | 0.041 · 0.0001 · 0.012 | >0.1 · 0.0003 · 0.03 |
| E · F · DG | 0.02 · 0.005 · 0.005 | 0.14 · 0.041 · 0.041 | 0.04 · 0.013 · 0.013 | >0.1 · 0.03 · 0.03 |
| E · R · DG | 0.013 · 0.001 · 0.004 | 0.086 · 0.004 · 0.026 | 0.043 · 0.002 · 0.013 | >0.1 · 0.005 · 0.03 |
| E · Q · DF | 0.018 · 0.0001 · 0.005 | >0.1 · 0.0003 · 0.03 | >0.1 · 0.0003 · 0.03 | >0.1 · 0.0003 · 0.03 |
| E · F · DF | 0.029 · 0.009 · 0.009 | >0.1 · 0.03 · 0.03 | >0.1 · 0.03 · 0.03 | >0.1 · 0.03 · 0.03 |
| E · R · DF | 0.016 · 0.001 · 0.005 | 0.084 · 0.004 · 0.025 | >0.1 · 0.005 · 0.03 | >0.1 · 0.005 · 0.03 |

P. g., *Porphyromonas gingivalis*;
UA159, *Streptococcus mutans*;
P. a., *Pseudomonas aeruginosa*;
S. a., *Staphylococcus aureus*
$IC_{50}$, concentrations of 50% inhibition on bacterial proliferation.
**The concentrations of metal ions are expressed in mM

TABLE 7

Antibacterial effects of novel regimens containing antibiotics.

| | $IC_{50}$ (mg/ml · mg/ml · mM) | | | |
|---|---|---|---|---|
| Drugs | P. g. | UA159 | P. a. | S. a. |
| E · Tb · Cu | 0.021 · 0.001 · 0.006 | <0.01 · 0.0003 · 0.003 | 0.118 · 0.004 · 0.035 | 0.010 · 0.0003 · 0.003 |
| E · Tb · Mn | 0.018 · 0.001 · 0.005 | <0.01 · 0.0003 · 0.003 | 0.077 · 0.002 · 0.023 | 0.009 · 0.0003 · 0.003 |
| E · Tb · Zn | 0.017 · 0.001 · 0.005 | <0.01 · 0.0003 · 0.003 | 0.113 · 0.003 · 0.034 | 0.010 · 0.0003 · 0.003 |
| C · Tb · Mn | 0.016 · 0.001 · 0.005 | <0.01 · 0.0003 · 0.003 | >0.1 · 0.003 · 0.03 | 0.009 · 0.0003 · 0.003 |
| C · Tb · Zn | 0.017 · 0.001 · 0.005 | <0.01 · 0.0003 · 0.003 | >0.1 · 0.03 · 0.03 | 0.011 · 0.0003 · 0.003 |
| E · Ny · Cu | 0.025 · 0.001 · 0.007 | >0.1 · 0.003 · 0.03 | >0.1 · 0.003 · 0.03 | >0.1 · 0.003 · 0.03 |
| E · Ny · Mn | 0.024 · 0.001 · 0.007 | >0.1 · 0.03 · 0.03 | 0.088 · 0.003 · 0.027 | >0.1 · 0.003 · 0.03 |
| E · Ny · Zn | 0.022 · 0.001 · 0.007 | >0.1 · 0.03 · 0.03 | 0.057 · 0.002 · 0.017 | >0.1 · 0.003 · 0.03 |
| C · Ny · Mn | 0.035 · 0.001 · 0.010 | 0.053 · 0.002 · 0.016 | >0.1 · 0.003 · 0.03 | 0.040 · 0.001 · 0.012 |
| C · Ny · Zn | 0.028 · 0.001 · 0.008 | 0.039 · 0.001 · 0.012 | >0.1 · 0.003 · 0.03 | 0.039 · 0.001 · 0.012 |
| E · PM · Cu | 0.025 · 0.001 · 0.008 | 0.059 · 0.002 · 0.018 | 0.025 · 0.001 · 0.008 | >0.1 · 0.003 · 0.03 |
| E · PM · Mn | 0.020 · 0.001 · 0.006 | 0.051 · 0.002 · 0.015 | 0.025 · 0.001 · 0.007 | >0.1 · 0.003 · 0.03 |
| E · PM · Zn | 0.017 · 0.001 · 0.005 | 0.058 · 0.002 · 0.017 | 0.025 · 0.001 · 0.007 | >0.1 · 0.003 · 0.03 |
| C · PM · Cu | 0.040 · 0.001 · 0.012 | 0.052 · 0.002 · 0.016 | 0.025 · 0.001 · 0.007 | 0.055 · 0.002 · 0.016 |
| C · PM · Mn | 0.027 · 0.001 · 0.008 | 0.075 · 0.002 · 0.022 | 0.028 · 0.001 · 0.009 | 0.046 · 0.001 · 0.014 |
| C · PM · Zn | 0.023 · 0.001 · 0.007 | 0.107 · 0.003 · 0.032 | 0.028 · 0.001 · 0.008 | 0.045 · 0.001 · 0.014 |
| G · INH · Cu | 0.045 · 0.001 · 0.013 | 0.035 · 0.001 · 0.011 | 0.078 · 0.002 · 0.023 | >0.1 · 0.003 · 0.03 |
| G · INH · Mn | 0.032 · 0.001 · 0.010 | 0.026 · 0.001 · 0.008 | 0.049 · 0.001 · 0.015 | >0.1 · 0.003 · 0.03 |
| G · INH · Zn | 0.036 · 0.001 · 0.011 | 0.019 · 0.001 · 0.006 | 0.062 · 0.001 · 0.019 | >0.1 · 0.003 · 0.03 |
| CC · INH · Cu | >0.1 · 0.003 · 0.03 | >0.1 · 0.003 · 0.03 | >0.1 · 0.003 · 0.03 | >0.1 · 0.003 · 0.03 |
| CC · INH · Mn | >0.1 · 0.003 · 0.03 | >0.1 · 0.003 · 0.03 | >0.1 · 0.003 · 0.03 | >0.1 · 0.003 · 0.03 |
| CC · INH · Zn | >0.1 · 0.003 · 0.03 | 0.029 · 0.001 · 0.009 | >0.1 · 0.003 · 0.03 | >0.1 · 0.003 · 0.03 |

P. g., *Porphyromonas gingivalis*;
UA159, *Streptococcus mutans*;
P. a., *Pseudomonas aeruginosa*;
S. a., *Staphylococcus aureus*
$IC_{50}$, concentrations of 50% inhibition on bacterial proliferation.

TABLE 8

Antibacterial effects of norvel regimens containing rifampin and streptomycin.

| Drugs | IC$_{50}$ (mg/ml · mg/ml · mM) | | | |
|---|---|---|---|---|
| | P. g. | UA159 | P. a. | S. a. |
| E · Rf · Cu | 0.0008 · 0.0002 · 0.0002 | 0.7 × 10$^{-4}$ · 0.2 × 10$^{-4}$ · 0.2 × 10$^{-4}$ | 0.039 · 0.012 · 0.012 | 0.0005 · 0.0001 · 0.0001 |
| E · Rf · Mn | 0.0005 · 0.0001 · 0.0001 | 0.4 × 10$^{-4}$ · 0.1 × 10$^{-4}$ · 0.1 × 10$^{-4}$ | 0.034 · 0.01 · 0.01 | 0.0003 · 0.0001 · 0.0001 |
| E · Rf · Zn | 0.0006 · 0.0002 · 0.0002 | 0.0002 · 0.0001 · 0.0001 | 0.032 · 0.01 · 0.01 | 0.0003 · 0.0001 · 0.0001 |
| C · Rf · Cu | 0.0004 · 0.0001 · 0.0001 | 0.4 × 10$^{-4}$ · 10$^{-5}$ · 10$^{-5}$ | 0.028 · 0.009 · 0.009 | 0.52 × 10$^{-4}$ · 0.16 × 10$^{-4}$ · 0.16 × 10$^{-4}$ |
| C · Rf · Mn | 0.0004 · 0.0001 · 0.0001 | 0.4 × 10$^{-4}$ · 10$^{-5}$ · 10$^{-5}$ | 0.043 · 0.013 · 0.013 | 0.57 × 10$^{-4}$ · 0.17 × 10$^{-4}$ · 0.17 × 10$^{-4}$ |
| C · Rf · Zn | 0.0004 · 0.0001 · 0.0001 | 0.4 × 10$^{-4}$ · 10$^{-5}$ · 10$^{-5}$ | 0.030 · 0.009 · 0.009 | 0.52 × 10$^{-4}$ · 0.16 × 10$^{-4}$ · 0.16 × 10$^{-4}$ |
| G · Rf · Cu | 0.001 · 0.0002 · 0.0002 | 0.0005 · 0.0001 · 0.0001 | 0.101 · 0.015 · 0.015 | 0.0005 · 0.0001 · 0.0001 |
| G · Rf · Mn | 0.001 · 0.0002 · 0.0002 | 0.0005 · 0.0001 · 0.0001 | 0.062 · 0.009 · 0.009 | 0.0006 · 0.0001 · 0.0001 |
| G · Rf · Zn | 0.001 · 0.0002 · 0.0002 | 0.0004 · 0.0001 · 0.0001 | 0.066 · 0.01 · 0.01 | 0.0005 · 0.0001 · 0.0001 |
| CC · Rf · Cu | 0.0005 · 0.0001 · 0.0001 | 0.4 × 10$^{-4}$ · 10$^{-5}$ · 10$^{-5}$ | 0.053 · 0.016 · 0.016 | 0.48 × 10$^{-4}$ · 0.14 × 10$^{-4}$ · 0.14 × 10$^{-4}$ |
| CC · Rf · Mn | 0.0004 · 0.0001 · 0.0001 | 0.4 × 10$^{-4}$ · 10$^{-5}$ · 10$^{-5}$ | 0.050 · 0.015 · 0.015 | 0.78 × 10$^{-4}$ · 0.23 × 10$^{-4}$ · 0.23 × 10$^{-4}$ |
| CC · Rf · Zn | 0.0004 · 0.0001 · 0.0001 | 0.4 × 10$^{-4}$ · 10$^{-5}$ · 10$^{-5}$ | 0.053 · 0.016 · 0.016 | 0.47 × 10$^{-4}$ · 0.14 × 10$^{-4}$ · 0.14 × 10$^{-4}$ |
| E · St · Cu | 0.020 · 0.006 · 0.006 | 0.035 · 0.011 · 0.011 | 0.018 · 0.005 · 0.005 | 0.032 · 0.010 · 0.010 |
| E · St · Mn | 0.016 · 0.005 · 0.005 | 0.038 · 0.011 · 0.011 | 0.022 · 0.006 · 0.006 | 0.047 · 0.014 · 0.014 |
| E · St · Zn | 0.017 · 0.005 · 0.005 | 0.041 · 0.012 · 0.012 | 0.026 · 0.008 · 0.008 | 0.030 · 0.009 · 0.009 |
| C · St · Cu | 0.016 · 0.005 · 0.005 | 0.017 · 0.005 · 0.005 | 0.028 · 0.009 · 0.009 | 0.005 · 0.001 · 0.001 |
| C · St · Mn | 0.015 · 0.005 · 0.005 | 0.029 · 0.009 · 0.009 | 0.032 · 0.010 · 0.010 | 0.025 · 0.008 · 0.008 |
| C · St · Zn | 0.016 · 0.005 · 0.005 | 0.022 · 0.007 · 0.007 | 0.031 · 0.010 · 0.010 | 0.032 · 0.010 · 0.010 |
| G · St · Cu | 0.027 · 0.004 · 0.004 | 0.083 · 0.012 · 0.012 | 0.063 · 0.010 · 0.010 | 0.089 · 0.013 · 0.013 |
| G · St · Mn | 0.021 · 0.003 · 0.003 | 0.082 · 0.012 · 0.012 | 0.047 · 0.007 · 0.007 | 0.063 · 0.010 · 0.010 |
| G · St · Zn | 0.024 · 0.004 · 0.004 | 0.052 · 0.008 · 0.008 | 0.047 · 0.007 · 0.007 | 0.078 · 0.012 · 0.012 |
| CC · St · Cu | 0.020 · 0.006 · 0.006 | 0.042 · 0.013 · 0.013 | 0.022 · 0.007 · 0.007 | 0.034 · 0.010 · 0.010 |
| CC · St · Mn | 0.015 · 0.005 · 0.005 | 0.041 · 0.013 · 0.013 | 0.027 · 0.008 · 0.008 | 0.035 · 0.011 · 0.011 |
| CC · St · Zn | 0.012 · 0.004 · 0.004 | 0.037 · 0.011 · 0.011 | 0.030 · 0.009 · 0.009 | 0.035 · 0.011 · 0.011 |

P. g., *Porphyromonas gingivalis*;
UA159, *Streptococcus mutans*;
P. a., *Pseudomonas aeruginosa*;
S. a., *Staphylococcus aureus*
IC$_{50}$, concentrations of 50% inhibition on bacterial proliferation.

TABLE 9

Antibacterial effects of novel regimens containing polypeptides.

| Drugs | IC$_{50}$ (mg/ml · mg/ml · mg/ml) | | | |
|---|---|---|---|---|
| | P. g. | UA159 | P. a. | S. a. |
| E · Q · PR | 0.01 · 0.00001 · 0.001 | 0.254 · 0.0003 · 0.025 | 0.073 · 0.0001 · 0.007 | >0.3 · 0.0003 · 0.03 |
| E · F · PR | 0.004 · 0.0004 · 0.0004 | 0.268 · 0.027 · 0.027 | 0.090 · 0.009 · 0.009 | >0.3 · 0.03 · 0.03 |
| E · R · PR | 0.007 · 0.0001 · 0.0007 | 0.128 · 0.001 · 0.013 | 0.089 · 0.001 · 0.009 | >0.3 · 0.003 · 0.03 |
| E · Q · Pro | 0.008 · 0.00001 · 0.0008 | 0.116 · 0.0001 · 0.012 | 0.080 · 0.0001 · 0.008 | >0.3 · 0.0003 · 0.03 |
| E · F · Pro | 0.007 · 0.0007 · 0.0007 | 0.092 · 0.009 · 0.009 | 0.076 · 0.008 · 0.008 | >0.3 · 0.03 · 0.03 |
| E · R · Pro | 0.008 · 0.0001 · 0.0008 | 0.107 · 0.001 · 0.011 | 0.076 · 0.001 · 0.008 | >0.3 · 0.003 · 0.03 |
| E · Q · PK84 | 0.006 · 0.00001 · 0.0006 | 0.198 · 0.0002 · 0.020 | 0.112 · 0.0001 · 0.011 | >0.3 · 0.0003 · 0.03 |
| E · F · PK84 | 0.003 · 0.0003 · 0.0003 | 0.152 · 0.015 · 0.015 | 0.104 · 0.010 · 0.010 | >0.3 · 0.03 · 0.03 |
| E · R · PK84 | 0.004 · 0.00004 · 0.0004 | 0.124 · 0.0012 · 0.012 | 0.084 · 0.0008 · 0.008 | >0.3 · 0.003 · 0.03 |
| E · Q · PK37 | 0.006 · 0.00001 · 0.0006 | 0.130 · 0.0001 · 0.013 | 0.088 · 0.0001 · 0.009 | >0.3 · 0.0003 · 0.03 |
| E · F · PK37 | 0.012 · 0.0012 · 0.0012 | 0.148 · 0.015 · 0.015 | 0.087 · 0.009 · 0.009 | >0.3 · 0.03 · 0.03 |
| E · R · PK37 | 0.008 · 0.0001 · 0.0008 | 0.101 · 0.001 · 0.010 | 0.080 · 0.001 · 0.008 | >0.3 · 0.003 · 0.03 |

TABLE 9-continued

Antibacterial effects of novel regimens containing polypeptides.

| | IC$_{50}$ (mg/ml · mg/ml · mg/ml) | | | |
|---|---|---|---|---|
| Drugs | P. g. | UA159 | P. a. | S. a. |
| E · Q · RF | 0.016 · 0.0001 · 0.003 | 0.089 · 0.0003 · 0.015 | 0.042 · 0.0001 · 0.007 | 0.040 · 0.0001 · 0.007 |
| E · F · RF | 0.016 · 0.005 · 0.003 | 0.081 · 0.024 · 0.014 | 0.049 · 0.015 · 0.008 | 0.042 · 0.013 · 0.007 |
| E · R · RF | 0.010 · 0.001 · 0.002 | 0.024 · 0.001 · 0.004 | 0.066 · 0.003 · 0.011 | 0.046 · 0.002 · 0.008 |
| E · Q · NTX | 0.023 · 0.0001 · 0.0007 | >0.1 · 0.0003 · 0.003 | 0.077 · 0.0002 · 0.002 | >0.1 · 0.0003 · 0.003 |
| E · F · NTX | 0.019 · 0.0058 · 0.0006 | >0.1 · 0.03 · 0.003 | 0.074 · 0.022 · 0.002 | >0.1 · 0.03 · 0.003 |
| E · R · NTX | 0.024 · 0.0012 · 0.0007 | 0.046 · 0.0023 · 0.0014 | 0.079 · 0.004 · 0.002 | >0.1 · 0.005 · 0.003 |
| E · Q · PLA2 | 0.022 · 0.0001 · 0.0007 | >0.1 · 0.0003 · 0.003 | 0.080 · 0.0002 · 0.002 | >0.1 · 0.0003 · 0.003 |
| E · F · PLA2 | 0.021 · 0.0064 · 0.0006 | >0.1 · 0.03 · 0.003 | 0.094 · 0.028 · 0.003 | >0.1 · 0.03 · 0.003 |
| E · R · PLA2 | 0.017 · 0.0009 · 0.0005 | 0.057 · 0.0028 · 0.0017 | 0.122 · 0.006 · 0.004 | >0.1 · 0.005 · 0.003 |
| E · Q · CTX14 | 0.019 · 0.0001 · 0.0006 | 0.116 · 0.0003 · 0.0035 | 0.094 · 0.0003 · 0.003 | >0.1 · 0.0003 · 0.003 |
| E · F · CTX14 | 0.015 · 0.0044 · 0.0004 | >0.1 · 0.03 · 0.003 | 0.083 · 0.025 · 0.002 | >0.1 · 0.03 · 0.003 |
| E · R · CTX14 | 0.018 · 0.0009 · 0.0005 | 0.041 · 0.002 · 0.001 | 0.085 · 0.004 · 0.003 | >0.1 · 0.005 · 0.003 |
| E · Q · α-BuTx | 0.021 · 0.0001 · 0.0006 | >0.1 · 0.0003 · 0.003 | 0.081 · 0.0002 · 0.002 | >0.1 · 0.0003 · 0.003 |
| E · F · α-BuTx | 0.021 · 0.0062 · 0.0006 | 0.119 · 0.036 · 0.004 | 0.070 · 0.021 · 0.002 | >0.1 · 0.03 · 0.003 |
| E · R · α-BuTx | 0.016 · 0.0008 · 0.0005 | 0.042 · 0.002 · 0.001 | 0.075 · 0.004 · 0.002 | >0.1 · 0.005 · 0.003 |

P. g., *Porphyromonas gingivalis*;
UA159, *Streptococcus mutans*;
P. a., *Pseudomonas aeruginosa*;
S. a., *Staphylococcus aureus*
IC$_{50}$, concentrations of 50% inhibition on bacterial proliferation.

TABLE 10

Antibacterial effects of novel regimens containing polypeptides.

| | IC$_{50}$ (mg/ml · mg/ml · mM) | | | |
|---|---|---|---|---|
| Drugs | P. g. | UA159 | P. a. | S. a. |
| E · PR · Cu | 0.025 · 0.008 · 0.008 | 0.067 · 0.020 · 0.020 | 0.061 · 0.018 · 0.018 | >0.1 · 0.03 · 0.03 |
| E · PR · Mn | 0.019 · 0.006 · 0.006 | >0.1 · 0.03 · 0.03 | 0.066 · 0.020 · 0.020 | >0.1 · 0.03 · 0.03 |
| E · PR · Zn | 0.022 · 0.007 · 0.007 | >0.1 · 0.03 · 0.03 | 0.054 · 0.016 · 0.016 | >0.1 · 0.03 · 0.03 |
| E · Pro · Cu | 0.020 · 0.006 · 0.006 | >0.1 · 0.03 · 0.03 | 0.050 · 0.015 · 0.015 | >0.1 · 0.03 · 0.03 |
| E · Pro · Mn | 0.016 · 0.005 · 0.005 | >0.1 · 0.03 · 0.03 | 0.055 · 0.016 · 0.016 | >0.1 · 0.03 · 0.03 |
| E · Pro · Zn | 0.018 · 0.005 · 0.005 | >0.1 · 0.03 · 0.03 | 0.045 · 0.014 · 0.014 | >0.1 · 0.03 · 0.03 |
| E · RF · Cu | 0.034 · 0.010 · 0.010 | >0.1 · 0.03 · 0.03 | 0.103 · 0.031 · 0.031 | >0.1 · 0.03 · 0.03 |
| E · RF · Mn | 0.027 · 0.008 · 0.008 | >0.1 · 0.03 · 0.03 | 0.063 · 0.019 · 0.019 | >0.1 · 0.03 · 0.03 |
| E · RF · Zn | 0.024 · 0.007 · 0.007 | >0.1 · 0.03 · 0.03 | 0.060 · 0.018 · 0.018 | >0.1 · 0.03 · 0.03 |
| E · PK37 · Cu | 0.025 · 0.008 · 0.008 | >0.1 · 0.03 · 0.03 | >0.1 · 0.03 · 0.03 | >0.1 · 0.03 · 0.03 |
| E · PK37 · Mn | 0.018 · 0.005 · 0.005 | >0.1 · 0.03 · 0.03 | 0.083 · 0.025 · 0.025 | >0.1 · 0.03 · 0.03 |
| E · PK37 · Zn | 0.018 · 0.005 · 0.005 | >0.1 · 0.03 · 0.03 | 0.078 · 0.023 · 0.023 | >0.1 · 0.03 · 0.03 |
| E · CTX14 · Cu | 0.031 · 0.001 · 0.009 | 0.057 · 0.002 · 0.017 | 0.082 · 0.002 · 0.025 | >0.1 · 0.003 · 0.03 |
| E · CTX14 · Mn | 0.024 · 0.001 · 0.007 | >0.1 · 0.003 · 0.03 | 0.063 · 0.002 · 0.019 | >0.1 · 0.003 · 0.03 |
| E · CTX14 · Zn | 0.024 · 0.001 · 0.007 | >0.1 · 0.003 · 0.03 | 0.049 · 0.001 · 0.015 | >0.1 · 0.003 · 0.03 |
| E · α-BuTx · Cu | 0.024 · 0.001 · 0.007 | 0.068 · 0.002 · 0.020 | 0.081 · 0.002 · 0.024 | >0.1 · 0.003 · 0.03 |
| E · α-BuTx · Mn | 0.022 · 0.001 · 0.007 | >0.1 · 0.003 · 0.03 | 0.070 · 0.002 · 0.021 | >0.1 · 0.003 · 0.03 |
| E · α-BuTx · Zn | 0.020 · 0.001 · 0.006 | >0.1 · 0.003 · 0.03 | 0.050 · 0.002 · 0.015 | >0.1 · 0.003 · 0.03 |
| E · PLA2 · Cu | 0.022 · 0.001 · 0.007 | 0.053 · 0.002 · 0.016 | >0.1 · 0.003 · 0.03 | >0.1 · 0.003 · 0.03 |
| E · PLA2 · Mn | 0.019 · 0.001 · 0.006 | >0.1 · 0.003 · 0.03 | 0.092 · 0.003 · 0.027 | >0.1 · 0.003 · 0.03 |
| E · PLA2 · Zn | 0.019 · 0.001 · 0.006 | >0.1 · 0.003 · 0.03 | 0.071 · 0.002 · 0.021 | >0.1 · 0.003 · 0.03 |
| E · ML · Cu | 0.025 · 0.001 · 0.007 | 0.083 · 0.002 · 0.025 | >0.1 · 0.003 · 0.03 | >0.1 · 0.003 · 0.03 |
| E · ML · Mn | 0.018 · 0.001 · 0.005 | >0.1 · 0.003 · 0.03 | 0.088 · 0.003 · 0.026 | >0.1 · 0.003 · 0.03 |
| E · ML · Zn | 0.019 · 0.001 · 0.006 | 0.087 · 0.003 · 0.026 | 0.097 · 0.003 · 0.029 | >0.1 · 0.003 · 0.03 |

P. g., *Porphyromonas gingivalis*;
UA159, *Streptococcus mutans*;
P. a., *Pseudomonas aeruginosa*;
S. a., *Staphylococcus aureus*
IC$_{50}$, concentrations of 50% inhibition on bacterial proliferation.

TABLE 11

Antibacterial effects of memantine (Mem) and metformin (MF) regimens.

| | IC$_{50}$ (mg/ml · mg/ml · mM) | | | |
|---|---|---|---|---|
| Drugs | P. g. | UA159 | P. a. | S. a. |
| E · Mem · Cu* | 0.028 · 0.028 · 0.028 | 0.276 · 0.276 · 0.276 | 0.073 · 0.073 · 0.073 | 0.089 · 0.089 · 0.089 |
| E · Mem · Ag* | 0.014 · 0.014 · 0.009 | 0.325 · 0.325 · 0.218 | 0.066 · 0.066 · 0.066 | >0.1 · 0.1 · 0.1 |
| E · Mem · Mn | 0.071 · 0.071 · 0.071 | 0.146 · 0.146 · 0.146 | 0.118 · 0.118 · 0.118 | 0.060 · 0.060 · 0.060 |
| E · Mem · VO$_4$ | 0.022 · 0.022 · 0.022 | >0.1 · 0.1 · 0.1 | >0.1 · 0.1 · 0.1 | >0.1 · 0.1 · 0.1 |
| E · Mem · Zn* | 0.065 · 0.065 · 0.065 | 0.092 · 0.092 · 0.092 | 0.071 · 0.071 · 0.071 | >0.1 · 0.1 · 0.1 |
| E · Mem · Sr | 0.075 · 0.075 · 0.226 | 0.110 · 0.110 · 0.329 | 0.155 · 0.155 · 0.464 | >0.1 · 0.1 · 0.3 |
| C · Mem · Cu | 0.062 · 0.062 · 0.019 | | 0.036 · 0.011 · 0.011 | 0.060 · 0.018 · 0.018 |
| C · Mem · Ag | 0.032 · 0.032 · 0.003 | | | |
| C · Mem · Mn | 0.037 · 0.037 · 0.011 | | 0.090 · 0.027 · 0.027 | 0.049 · 0.015 · 0.015 |
| C · Mem · VO$_4$ | 0.048 · 0.048 · 0.014 | | | |
| C · Mem · Zn | 0.047 · 0.047 · 0.014 | | | |
| C · Mem · Sr | 0.041 · 0.041 · 0.041 | | | |
| E · MF · Cu* | 0.050 · 0.015 · 0.050 | 0.094 · 0.094 · 0.094 | 0.623 · 0.187 · 0.623 | >0.1 · 0.03 · 0.1 |
| E · MF · Se* | 0.040 · 0.012 · 0.040 | 0.042 · 0.042 · 0.042 | 0.090 · 0.027 · 0.090 | >0.1 · 0.03 · 0.1 |
| E · MF · Mn* | 0.060 · 0.018 · 0.060 | >0.1 · 0.03 · 0.1 | >0.1 · 0.03 · 0.1 | 0.044 · 0.013 · 0.044 |
| E · MF · VO$_4$* | 0.037 · 0.011 · 0.037 | 0.259 · 0.078 · 0.259 | >0.1 · 0.03 · 0.1 | >0.1 · 0.03 · 0.1 |
| E · MF · Zn* | 0.066 · 0.020 · 0.066 | 0.259 · 0.078 · 0.259 | >0.1 · 0.03 · 0.1 | >0.1 · 0.03 · 0.1 |
| E · MF · Sr* | 0.097 · 0.029 · 0.292 | >0.1 · 0.03 · 0.3 | >0.1 · 0.03 · 0.3 | >0.1 · 0.03 · 0.3 |
| C · MF · Cu | >0.03 · 0.03 · 0.1 | | 0.046 · 0.046 · 0.014 | 0.042 · 0.042 · 0.013 |
| C · MF · Ag | 0.008 · 0.008 · 0.017 | | | |
| C · MF · Mn | >0.03 · 0.03 · 0.1 | | 0.066 · 0.066 · 0.020 | 0.047 · 0.047 · 0.014 |
| C · MF · VO$_4$ | >0.03 · 0.03 · 0.1 | | | |
| C · MF · Zn* | >0.03 · 0.03 · 0.1 | | | |
| C · MF · Sr | >0.03 · 0.03 · 0.3 | | | |
| G · Mem · Cu* | 0.032 · 0.005 · 0.005 | 0.022 · 0.003 · 0.003 | 0.205 · 0.031 · 0.031 | >0.2 · 0.03 · 0.03 |
| G · Mem · Ag* | 0.023 · 0.003 · 0.001 | 0.013 · 0.002 · 0.001 | 0.103 · 0.015 · 0.005 | >0.2 · 0.03 · 0.01 |
| G · Mem · Mn* | 0.030 · 0.005 · 0.005 | 0.061 · 0.009 · 0.009 | 0.112 · 0.017 · 0.017 | 0.095 · 0.014 · 0.014 |
| G · Mem · VO$_4$* | 0.046 · 0.007 · 0.007 | 0.072 · 0.011 · 0.011 | >0.2 · 0.03 · 0.03 | >0.2 · 0.03 · 0.03 |
| G · Mem · Zn* | 0.031 · 0.005 · 0.005 | 0.051 · 0.008 · 0.008 | 0.118 · 0.018 · 0.018 | >0.2 · 0.03 · 0.03 |
| G · Mem · Sr* | 0.036 · 0.005 · 0.018 | 0.059 · 0.009 · 0.029 | 0.114 · 0.017 · 0.057 | >0.2 · 0.03 · 0.1 |
| G · MF · Cu* | 0.042 · 0.021 · 0.006 | 0.146 · 0.073 · 0.022 | 0.138 · 0.070 · 0.021 | >0.2 · 0.1 · 0.03 |
| G · MF · Ag | 0.025 · 0.012 · 0.001 | >0.2 · 0.1 · 0.01 | 0.076 · 0.038 · 0.004 | >0.2 · 0.1 · 0.01 |
| G · MF · Mn* | 0.024 · 0.012 · 0.004 | >0.2 · 0.1 · 0.03 | 0.065 · 0.032 · 0.010 | 0.264 · 0.132 · 0.040 |
| G · MF · VO4 | 0.039 · 0.019 · 0.006 | >0.2 · 0.1 · 0.03 | >0.2 · 0.1 · 0.03 | >0.2 · 0.1 · 0.03 |
| G · MF · Zn* | 0.032 · 0.016 · 0.005 | 0.147 · 0.073 · 0.022 | 0.104 · 0.052 · 0.016 | >0.2 · 0.1 · 0.03 |
| G · MF · Sr | 0.027 · 0.013 · 0.013 | >0.2 · 0.1 · 0.1 | 0.077 · 0.038 · 0.038 | >0.2 · 0.1 · 0.1 |

*P. g.*, *Porphyromonas gingivalis*;
UA159, *Streptococcus mutans*;
*P. a.*, *Pseudomonas aeruginosa*;
*S. a.*, *Staphylococcus aureus*.
IC$_{50}$, concentrations of 50% inhibition on bacterial proliferation.
*The drug combinations listed in this table at concentrations of 3 to 10 times higher than the listed IC$_{50}$ have no inhibition on the proliferation of the cultured *Lactobacillus reuteri*

TABLE 12

Antibacterial effects of norvel regimens containing natural products.

| | IC$_{50}$ (mg/ml · mg/ml · mM) | | | |
|---|---|---|---|---|
| Drugs | P. g. | UA159 | P. a. | S. a. |
| E · Bb · Cu | 0.020 · 0.006 · 0.006 | 0.035 · 0.011 · 0.011 | 0.080 · 0.024 · 0.024 | >0.1 · 0.03 · 0.03 |
| E · Bb · Mn | 0.018 · 0.005 · 0.005 | 0.037 · 0.011 · 0.011 | 0.063 · 0.019 · 0.019 | >0.1 · 0.03 · 0.03 |
| E · Bb · Zn | 0.017 · 0.005 · 0.005 | 0.039 · 0.012 · 0.012 | 0.064 · 0.019 · 0.019 | >0.1 · 0.03 · 0.03 |
| C · Bb · Cu | 0.069 · 0.021 · 0.021 | 0.036 · 0.011 · 0.011 | >0.1 · 0.03 · 0.03 | 0.031 · 0.009 · 0.009 |
| C · Bb · Mn | 0.039 · 0.012 · 0.012 | 0.054 · 0.016 · 0.016 | >0.1 · 0.03 · 0.03 | 0.036 · 0.011 · 0.011 |
| C · Bb · Zn | 0.034 · 0.010 · 0.010 | 0.044 · 0.013 · 0.013 | >0.1 · 0.03 · 0.03 | 0.032 · 0.010 · 0.010 |
| G · Bb · Mn | 0.028 · 0.004 · 0.004 | 0.091 · 0.014 · 0.014 | 0.238 · 0.036 · 0.036 | >0.2 · 0.03 · 0.03 |
| G · Bb · Zn | 0.013 · 0.002 · 0.002 | 0.076 · 0.011 · 0.011 | 0.116 · 0.017 · 0.017 | >0.2 · 0.03 · 0.03 |
| E · Qc · Cu | 0.020 · 0.006 · 0.006 | 0.069 · 0.021 · 0.021 | 0.084 · 0.023 · 0.023 | >0.1 · 0.03 · 0.03 |
| E · Qc · Mn | 0.015 · 0.005 · 0.005 | 0.087 · 0.026 · 0.026 | 0.054 · 0.016 · 0.016 | >0.1 · 0.03 · 0.03 |
| E · Qc · Zn | 0.015 · 0.004 · 0.004 | >0.1 · 0.03 · 0.03 | 0.063 · 0.019 · 0.019 | >0.1 · 0.03 · 0.03 |
| C · Qc · Cu | 0.037 · 0.011 · 0.011 | 0.149 · 0.045 · 0.045 | >0.1 · 0.03 · 0.03 | >0.1 · 0.03 · 0.03 |
| C · Qc · Mn | 0.027 · 0.008 · 0.008 | 0.076 · 0.023 · 0.023 | >0.1 · 0.03 · 0.03 | >0.1 · 0.03 · 0.03 |
| C · Qc · Zn | 0.023 · 0.007 · 0.007 | 0.086 · 0.026 · 0.026 | >0.1 · 0.03 · 0.03 | >0.1 · 0.03 · 0.03 |
| G · Qc · Mn | 0.026 · 0.004 · 0.004 | 0.117 · 0.018 · 0.018 | 0.131 · 0.020 · 0.020 | >0.2 · 0.03 · 0.03 |
| G · Qc · Zn | 0.018 · 0.003 · 0.003 | 0.078 · 0.012 · 0.012 | 0.119 · 0.018 · 0.018 | >0.2 · 0.03 · 0.03 |
| E · TMP · Cu | 0.017 · 0.005 · 0.005 | 0.094 · 0.028 · 0.028 | 0.053 · 0.016 · 0.016 | >0.1 · 0.03 · 0.03 |
| E · TMP · Mn | 0.013 · 0.004 · 0.004 | >0.1 · 0.03 · 0.03 | 0.054 · 0.016 · 0.016 | >0.1 · 0.03 · 0.03 |

TABLE 12-continued

Antibacterial effects of norvel regimens containing natural products.

| | IC$_{50}$ (mg/ml · mg/ml · mM) | | | |
|---|---|---|---|---|
| Drugs | P. g. | UA159 | P. a. | S. a. |
| E · TMP · Zn | 0.014 · 0.004 · 0.004 | >0.1 · 0.03 · 0.03 | 0.038 · 0.011 · 0.011 | >0.1 · 0.03 · 0.03 |
| C · TMP · Cu | 0.015 · 0.005 · 0.005 | 0.045 · 0.013 · 0.013 | 0.063 · 0.019 · 0.019 | 0.048 · 0.014 · 0.014 |
| C · TMP · Mn | 0.010 · 0.003 · 0.003 | 0.037 · 0.011 · 0.011 | 0.042 · 0.013 · 0.013 | 0.059 · 0.018 · 0.018 |
| C · TMP · Zn | 0.011 · 0.003 · 0.003 | 0.029 · 0.009 · 0.009 | 0.051 · 0.015 · 0.015 | 0.048 · 0.014 · 0.014 |
| G · TMP · Cu | 0.026 · 0.008 · 0.008 | >0.1 · 0.03 · 0.03 | >0.1 · 0.03 · 0.03 | >0.1 · 0.03 · 0.03 |
| G · TMP · Mn | 0.017 · 0.005 · 0.005 | 0.052 · 0.016 · 0.016 | >0.1 · 0.03 · 0.03 | >0.1 · 0.03 · 0.03 |
| G · TMP · Zn | 0.017 · 0.005 · 0.005 | 0.024 · 0.007 · 0.007 | 0.083 · 0.025 · 0.025 | >0.1 · 0.03 · 0.03 |
| CC · TMP · Cu | 0.030 · 0.009 · 0.009 | >0.1 · 0.03 · 0.03 | >0.1 · 0.03 · 0.03 | >0.1 · 0.03 · 0.03 |
| CC · TMP · Mn | 0.017 · 0.005 · 0.005 | >0.1 · 0.03 · 0.03 | >0.1 · 0.03 · 0.03 | 0.100 · 0.030 · 0.030 |
| CC · TMP · Zn | 0.025 · 0.007 · 0.007 | 0.087 · 0.026 · 0.026 | >0.1 · 0.03 · 0.03 | 0.074 · 0.022 · 0.022 |
| E · NDGA · Cu | 0.015 · 0.004 · 0.004 | 0.037 · 0.011 · 0.011 | 0.040 · 0.012 · 0.012 | >0.1 · 0.03 · 0.03 |
| E · NDGA · Mn | 0.014 · 0.004 · 0.004 | 0.033 · 0.010 · 0.010 | 0.040 · 0.012 · 0.012 | >0.1 · 0.03 · 0.03 |
| E · NDGA · Zn | 0.014 · 0.004 · 0.004 | 0.033 · 0.010 · 0.010 | 0.039 · 0.012 · 0.012 | >0.1 · 0.03 · 0.03 |
| C · NDGA · Cu | 0.018 · 0.005 · 0.005 | 0.030 · 0.009 · 0.009 | 0.131 · 0.039 · 0.039 | 0.030 · 0.009 · 0.009 |
| C · NDGA · Mn | 0.012 · 0.004 · 0.004 | 0.032 · 0.010 · 0.010 | 0.049 · 0.015 · 0.015 | 0.058 · 0.017 · 0.017 |
| C · NDGA · Zn | 0.011 · 0.003 · 0.003 | 0.035 · 0.010 · 0.010 | 0.051 · 0.015 · 0.015 | 0.049 · 0.015 · 0.015 |
| G · NDGA · Cu | 0.022 · 0.007 · 0.007 | <0.01 · 0.003 · 0.003 | >0.1 · 0.03 · 0.03 | >0.1 · 0.03 · 0.03 |
| G · NDGA · Mn | 0.019 · 0.006 · 0.006 | 0.020 · 0.006 · 0.006 | 0.070 · 0.021 · 0.021 | >0.1 · 0.03 · 0.03 |
| G · NDGA · Zn | 0.018 · 0.005 · 0.005 | 0.020 · 0.006 · 0.006 | 0.074 · 0.022 · 0.022 | >0.1 · 0.03 · 0.03 |
| CC · NDGA · Cu | 0.034 · 0.010 · 0.010 | <0.01 · 0.003 · 0.003 | >0.1 · 0.03 · 0.03 | 0.053 · 0.016 · 0.016 |
| CC · NDGA · Mn | 0.021 · 0.006 · 0.006 | 0.038 · 0.011 · 0.011 | >0.1 · 0.03 · 0.03 | >0.01 · 0.003 · 0.003 |
| CC · NDGA · Zn | 0.025 · 0.008 · 0.008 | 0.031 · 0.009 · 0.009 | >0.1 · 0.03 · 0.03 | 0.043 · 0.013 · 0.013 |

*P. g.*, Porphyromonas gingivalis;
UA159, Streptococcus mutans;
*P. a.*, Pseudomonas aeruginosa;
*S. a.*, Staphylococcus aureus.
IC$_{50}$, concentrations of 50% inhibition on bacterial proliferation.

TABLE 13

Antibacterial effects of novel regimens containing etidronate (Eti), glibenclamide (Gbc) or 3,4-diaminopysidine (3,4-DAP).

| | IC$_{50}$ (mg/ml · mg/ml · mM) | | | |
|---|---|---|---|---|
| Drugs | P. g. | UA159 | P. a. | S. a. |
| A. | | | | |
| E · Eti · Cu | 0.048 · 0.143 · 0.048 | 0.080 · 0.239 · 0.080 | >0.1 · 0.1 · 0.1 | 0.027 · 0.082 · 0.027 |
| E · Eti · Ag* | 0.019 · 0.057 · 0.019 | 0.145 · 0.436 · 0.044 | | |
| E · Eti · Mn | 0.037 · 0.112 · 0.037 | 0.632 · 1.895 · 0.632 | >0.1 · 0.1 · 0.1 | 0.022 · 0.067 · 0.022 |
| E · Eti · VO$_4$ | 0.051 · 0.152 · 0.051 | 0.087 · 0.260 · 0.087 | >0.1 · 0.1 · 0.1 | 0.028 · 0.085 · 0.028 |
| E · Eti · Zn | 0.042 · 0.126 · 0.042 | 0.169 · 0.508 · 0.169 | >0.1 · 0.1 · 0.1 | 0.036 · 0.107 · 0.036 |
| E · Eti · Sr | 0.04 · 0.128 · 0.13 | 2.81 · 8.443 · 8.44 | >0.1 · 0.1 · 0.3 | 0.02 · 0.069 · 0.07 |
| C · Eti · Cu | 0.037 · 0.110 · 0.011 | | >0.1 · 0.3 · 0.03 | 0.028 · 0.083 · 0.008 |
| C · Eti · Ag | 0.031 · 0.092 · 0.003 | | >0.1 · 0.3 · 0.01 | 0.026 · 0.079 · 0.008 |
| C · Eti · Mn | 0.032 · 0.095 · 0.009 | | >0.1 · 0.3 · 0.03 | 0.022 · 0.065 · 0.007 |
| C · Eti · VO$_4$ | 0.038 · 0.113 · 0.011 | | >0.1 · 0.3 · 0.03 | 0.044 · 0.131 · 0.013 |
| C · Eti · Zn | 0.038 · 0.115 · 0.012 | | >0.1 · 0.3 · 0.03 | 0.026 · 0.078 · 0.008 |
| C · Eti · Sr | 0.037 · 0.112 · 0.037 | | >0.1 · 0.3 · 0.1 | 0.029 · 0.088 · 0.029 |
| G · Eti · Cu* | 0.051 · 0.076 · 0.008 | 0.065 · 0.098 · 0.010 | >0.2 · 0.3 · 0.03 | >0.2 · 0.3 · 0.03 |
| G · Eti · Ag* | 0.030 · 0.045 · 0.001 | 0.041 · 0.062 · 0.002 | >0.2 · 0.3 · 0.01 | >0.2 · 0.3 · 0.01 |
| G · Eti · Mn* | 0.041 · 0.061 · 0.006 | 0.047 · 0.071 · 0.007 | >0.2 · 0.3 · 0.03 | >0.2 · 0.3 · 0.03 |
| G · Eti · VO$_4$* | 0.045 · 0.067 · 0.007 | 0.057 · 0.086 · 0.009 | >0.2 · 0.3 · 0.03 | >0.2 · 0.3 · 0.03 |
| G · Eti · Zn* | 0.046 · 0.068 · 0.007 | 0.052 · 0.078 · 0.008 | >0.2 · 0.3 · 0.03 | >0.2 · 0.3 · 0.03 |
| G · Eti · Sr* | 0.047 · 0.070 · 0.023 | 0.026 · 0.040 · 0.013 | >0.2 · 0.3 · 0.1 | >0.2 · 0.3 · 0.1 |
| B. | | | | |
| E · Gbc · Cu | 0.038 · 2.5 × 10$^{-4}$ · 0.038 | >0.1 · 6.6 × 10$^{-4}$ · 0.1 | 0.116 · 7.7 × 10$^{-4}$ · 0.116 | >0.1 · 6.6 × 10$^{-4}$ · 0.1 |
| E · Gbc · Se | 0.039 · 2.6 × 10$^{-4}$ · 0.039 | 0.040 · 2.7 × 10$^{-4}$ · 0.04 | 0.098 · 6.5 × 10$^{-4}$ · 0.098 | >0.1 · 6.6 × 10$^{-4}$ · 0.1 |
| E · Gbc · Mn | 0.084 · 5.5 × 10$^{-4}$ · 0.084 | >0.1 · 6.6 × 10$^{-4}$ · 0.1 | 0.097 · 6.4 × 10$^{-4}$ · 0.097 | 0.070 · 4.6 × 10$^{-4}$ · 0.07 |
| E · Gbc · VO$_4$ | >0.1 · 6.6 × 10$^{-4}$ · 0.1 | >0.1 · 6 × 10$^{-4}$ · 0.1 | >0.1 · 6.6 × 10$^{-4}$ · 0.1 | >0.1 · 6.6 × 10$^{-4}$ · 0.1 |
| E · Gbc · Zn | 0.074 · 4.9 × 10$^{-4}$ · 0.074 | >0.1 · 6.6 × 10$^{-4}$ · 0.1 | 0.096 · 6.4 × 10$^{-4}$ · 0.096 | >0.1 · 6.6 × 10$^{-4}$ · 0.1 |
| E · Gbc · Sr | 0.07 · 4.9 × 10$^{-4}$ · 0.22 | >0.1 · 6.6 × 10$^{-4}$ · 0.3 | 0.128 · 8.5 × 10$^{-4}$ · 0.385 | >0.1 · 6.6 × 10$^{-4}$ · 0.3 |
| E · 3,4DAP · Cu | 0.062 · 0.019 · 0.062 | >0.1 · 0.03 · 0.1 | 0.210 · 0.063 · 0.210 | >0.1 · 0.03 · 0.1 |

TABLE 13-continued

Antibacterial effects of novel regimens containing etidronate (Eti), glibenclamide (Gbc) or 3,4-diaminopysidine (3,4-DAP).

| | | | | |
|---|---|---|---|---|
| E · 3,4DAP · Se | 0.027 · 0.008 · 0.027 | 0.022 · 0.007 · 0.022 | 0.220 · 0.066 · 0.220 | >0.1 · 0.03 · 0.1 |
| E · 3,4DAP · Mn | 0.195 · 0.058 · 0.195 | >0.1 · 0.03 · 0.1 | >0.1 · 0.03 · 0.1 | >0.1 · 0.03 · 0.1 |
| E · 3,4DAP · VO$_4$ | 0.014 · 0.004 · 0.014 | >0.1 · 0.03 · 0.1 | >0.1 · 0.03 · 0.1 | >0.1 · 0.03 · 0.1 |
| E · 3,4DAP · Zn | >0.1 · 0.03 · 0.1 | >0.1 · 0.03 · 0.1 | 0.191 · 0.057 · 0.191 | >0.1 · 0.03 · 0.1 |
| E · 3,4DAP · Sr | >0.1 · 0.03 · 0.3 | >0.1 · 0.03 · 0.3 | 0.271 · 0.081 · 0.813 | >0.1 · 0.03 · 0.3 |

C.

| Drugs | IC$_{50}$ (mg/ml · mg/ml · mM · mg/ml) | |
|---|---|---|
| | P. g. | UA159 |
| E · Gbc · Zn · Mem | 0.047 · 3.1 × 10$^{-4}$ · 0.047 · 0.047 | >0.075 · 5 × 10$^{-4}$ · 0.075 · 0.075 |
| E · Gbc · Sr · Mem | 0.050 · 3.3 × 10$^{-4}$ · 0.050 · 0.050 | >0.075 · 5 × 10$^{-4}$ · 0.225 · 0.075 |
| E · Gbc · Ge · Mem | 0.049 · 3.3 × 10$^{-4}$ · 0.049 · 0.049 | >0.075 · 5 × 10$^{-4}$ · 0.025 · 0.075 |
| E · 3,4DAP · Cu · Mem | 0.020 · 0.007 · 0.020 · 0.020 | >0.075 · 0.025 · 0.075 · 0.075 |
| E · 3,4DAP · Mn · Mem | 0.023 · 0.008 · 0.023 · 0.023 | >0.075 · 0.025 · 0.075 · 0.075 |
| E · 3,4DAP · Zn · Mem | 0.024 · 0.008 · 0.024 · 0.024 | >0.075 · 0.025 · 0.075 · 0.075 |
| E · 3,4DAP · Sr · Mem | 0.021 · 0.007 · 0.021 · 0.021 | >0.075 · 0.025 · 0.225 · 0.075 |
| E · 3,4DAP · Ge · Mem | 0.018 · 0.006 · 0.018 · 0.018 | >0.075 · 0.025 · 0.025 · 0.075 |

P. g., *Porphyromonas gingivalis*;
UA159, *Streptococcus mutans*;
P. a., *Pseudomonas aeruginosa*;
S. a., *Staphylococcus aureus*
IC$_{50}$, concentrations of 50% inhibition on bacterial proliferation.
*The drug combinations listed in this table at concentrations of 3 to 10 times higher than the listed IC$_{50}$ have no inhibition on the proliferation of the cultured *Lactobacillus reuteri*

TABLE 14

Antibacterial effects of novel regimens cotaiming AgCl, Ge and cisplatin (Pt)..

| | IC$_{50}$ (mg/ml · mg/ml · mM) | | | |
|---|---|---|---|---|
| Drugs | P. g. | UA159 | P. a. | S. a. |
| A. | | | | |
| E · Q · Ag | 0.040 · 0.0001 · 0.007 | >0.1 · 0.0003 · 0.021 | 0.017 · 0.0001 · 0.007 | 0.017 · 0.0001 · 0.007 |
| E · F · Ag | 0.105 · 0.031 · 0.021 | 0.165 · 0.049 · 0.035 | 0.125 · 0.038 · 0.028 | 0.018 · 0.005 · 0.007 |
| E · R · Ag | 0.069 · 0.003 · 0.014 | 0.033 · 0.002 · 0.007 | 0.018 · 0.001 · 0.007 | 0.023 · 0.001 · 0.007 |
| E · Gbc · Ag | 0.185 · 1.22 × 10$^{-3}$ · 0.042 | 0.133 · 8.76 × 10$^{-4}$ · 0.028 | 0.017 · 1.12 × 10$^{-4}$ · 0.007 | >0.1 · 6.6 × 10$^{-4}$ · 0.021 |
| E · 34DAP · Ag | 0.042 · 0.013 · 0.007 | 0.149 · 0.045 · 0.028 | 0.016 · 0.005 · 0.007 | 0.021 · 0.006 · 0.004 |
| E · Mem · Ag | 0.041 · 0.041 · 0.007 | 0.149 · 0.149 · 0.028 | 0.019 · 0.019 · 0.007 | 0.044 · 0.044 · 0.007 |
| E · MF · Ag | 0.183 · 0.055 · 0.035 | 0.418 · 0.125 · 0.143 | 0.017 · 0.005 · 0.007 | >0.1 · 0.03 · 0.021 |
| E · CPZ · Ag | 0.026 · 0.008 · 0.007 | 0.034 · 0.010 · 0.007 | 0.017 · 0.005 · 0.007 | 0.024 · 0.007 · 0.007 |
| E · Eti · Ag | 0.029 · 0.086 · 0.007 | 0.115 · 0.344 · 0.021 | 0.021 · 0.064 · 0.007 | 0.050 · 0.151 · 0.014 |
| E · Clo · Ag | 0.058 · 0.175 · 0.014 | >0.1 · 0.3 · 0.021 | 0.186 · 0.559 · 0.042 | >0.1 · 0.3 · 0.021 |
| Ag | 0.014 mM | 0.035 mM | 0.042 mM | 0.056 mM |
| B. | | | | |
| E · Q · Ge | 1.269 · 0.0038 · 3.81 | >0.1 · 0.0003 · 0.3 | | |
| E · F · Ge | 0.199 · 0.060 · 0.596 | >0.1 · 0.03 · 0.3 | | |
| E · R · Ge | 0.046 · 0.002 · 0.139 | >0.1 · 0.005 · 0.3 | | |
| F · Q · Ge | >0.03 · 0.0003 · 0.3 | 0.815 · 0.008 · 8.15 | | |
| F · R · Ge | 0.037 · 0.006 · 0.371 | 0.3 · 0.05 · 2.99 | | |
| R · U · Ge | 0.005 · 0.030 · 0.295 | >0.005 · 0.03 · 0.3 | | |
| C. | | | | |
| E · Q · Pt | 0.039 · 0.0001 · 0.012 | >0.1 · 0.001 · 0.03 | 0.040 · 0.0001 · 0.012 | 0.041 · 0.0001 · 0.012 |
| E · R · Pt | 0.038 · 0.002 · 0.001 | 0.028 · 0.004 · 0.008 | 0.069 · 0.003 · 0.021 | 0.043 · 0.002 · 0.013 |
| E · Et · Pt | 0.046 · 0.0014 · 0.014 | >0.1 · 0.03 · 0.03 | | |
| E · Pt | 0.046 · 0.015 | 0.154 · 0.051 | | |

TABLE 14-continued

Antibacterial effects of novel regimens cotaiming AgCl, Ge and cisplatin (Pt)..

| Drugs | IC$_{50}$ (mg/ml · mg/ml · mM) | | | |
|---|---|---|---|---|
| | P. g. | UA159 | P. a. | S. a. |
| R · Pt | 0.005 · 0.003 | | | |
| Et | 0.125 mg/ml | >0.1 mg/ml | | |
| Pt | 0.069 mM | >0.1 mM | | |

P. g., Porphyromonas gingivalis;
UA159, Streptococcus mutans;
P. a., Pseudomonas aeruginosa;
S. a., Staphylococcus aureus
IC$_{50}$, concentrations of 50% inhibition on bacterial proliferation.

TABLE 15

Antibacterial effects of herbs-metallic compounds.

| Drugs | IC$_{50}$ (mg/ml · mg/ml · mM) | Potency | Av. Potency |
|---|---|---|---|
| A. Porphyromonas gingivalis | | | |
| E · GIM | 0.023 · 0.076 | 3.70 · 12.42 | 8 |
| E · GIM · Zn | 0.022 · 0.066 · 0.007 | 3.86 · 14.30 · 90.29 | 36 |
| E · OP | 0.022 · 0.022 | 6.86 · 13.64 | 9 |
| E · OP · Zn | 0.019 · 0.019 · 0.006 | 4.47 · 15.79 · 105.33 | 42 |
| T · GIM | 0.055 · 0.182 | 3.04 · 5.19 | 4 |
| T · GIM · Zn | 0.031 · 0.092 · 0.009 | 5.39 · 10.26 · 70.22 | 59 |
| T · OP | 0.036 · 0.036 | 4.64 · 8.33 | 6 |
| T · OP · Zn | 0.032 · 0.032 · 0.010 | 5.22 · 9.38 · 63.20 | 26 |
| G · GIM | 0.035 · 0.115 | 3.89 · 8.21 | 6 |
| G · GIM · Zn | 0.025 · 0.075 · 0.008 | 5.44 · 12.59 · 79 | 32 |
| G · OP | 0.030 · 0.030 | 4.53 · 10 | 7 |
| G · OP · Zn | 0.025 · 0.025 · 0.008 | 5.44 · 12 · 79 | 32 |
| B. Streptococcus mutans | | | |
| E · GIM | 0.067 · 0.224 | 2.04 · 4.46 | 3 |
| E · OP | 0.085 · 0.085 | 1.61 · 3.53 | 3 |
| G · GIM | 0.076 · 0.254 | 13.16 · 3.94 | 9 |
| G · OP | 0.059 · 0.059 | 16.95 · 5.08 | 11 |
| G · OP · Zn | 0.052 · 0.052 · 0.016 | 19.23 · 5.77 · 125 | 50 |
| T · GIM | 0.084 · 0.280 | 1.48 · 3.57 | 3 |
| T · GIM · Zn | 0.072 · 0.217 · 0.022 | 1.72 · 4.61 · 90.91 | 32 |
| T · OP · Zn | 0.049 · 0.049 · 0.015 | 2.53 · 6.12 · 133.33 | 47 |

IC$_{50}$, concentrations of 50% inhibition on bacterial proliferation.

TABLE 16

Selective antibacterial effects of novel regimens without inhibition on neuroblastoma SHSY5Y cells
IC$_{50}$ (mg/ml · mg/ml · mM)

| | SHSY5Y | P. g. | UA159 | E. Coli | B. s. | P. a. | S. a. | L. r. |
|---|---|---|---|---|---|---|---|---|
| C · MF · Cu | >0.03 · 0.03 · 0.1 | >0.03 · 0.03 · 0.1 | >0.1 · 0.1 · 0.03 | 0057 · 0057 · 0.017 | 0024 · 0024 · 0.007 | 0.046 · 0.046 · 0.014 | 0.042 · 0.042 · 0.013 | 0.213 · 0.213 · 0.064 |
| C · MF · VO$_4$ | >0.03 · 0.03 · 0.1 | >0.03 · 0.03 · 0.1 | | >0.03 · 0.03 · 0.1 | >0.03 · 0.03 · 0.1 | >0.03 · 0.03 · 0.1 | >0.03 · 0.03 · 0.1 | |
| C · MF · Zn | >0.03 · 0.03 · 0.1 | >0.03 · 0.03 · 0.1 | 0.027 · 0.027 · 0.008 | 0.049 · 0.049 · 0.015 | 0.031 · 0.031 · 0.009 | 0.061 · 0.061 · 0.018 | 0.030 · 0.030 · 0.009 | 0.027 · 0.027 · 0.008 |
| C · MF · Sr | >0.03 · 0.03 · 0.3 | >0.03 · 0.03 · 0.3 | | | | | | |
| E · TRZ · RuR | >0.3 · 0.03 · 0.04 | 0.024 · 0.001 · 0.002 | 0.114 · 0.004 · 0.013 | 0.090 · 0.003 · 0.010 | >0.3 · 0.03 · 0.04 | 0.047 · 0.002 · 0.006 | 0.143 · 0.005 · 0.016 | 0.249 · 0.008 · 0.029 |
| E · Eti · RuR | >0.03 · 0.3 · 0.04 | 0.0078 · 0.078 · 0.009 | 0.064 · 0.064 · 0.007 | 0.287 · 0.287 · 0.03 | 0.334 · 0.334 · 0.04 | 0.069 · 0.069 · 0.008 | 0.290 · 0.290 · 0.03 | >0.3 · 0.3 · 0.04 |
| E · Mem · Zn | >0.1 · 0.03 · 0.03 | 0.065 · 0.065 · 0.065 | 0.092 · 0.092 · 0.092 | 0.433 · 0.130 · 0.130 | >0.1 · 0.03 · 0.03 | 0.071 · 0.071 · 0.071 | >0.1 · 0.1 · 0.1 | >0.1 · 0.03 · 0.03 |
| G · CC · VO$_4$ | >0.2 · 0.1 · 0.03 | 0.049 · 0.025 · 0.007 | 0.204 · 0.120 · 0.036 | >0.2 · 0.1 · 0.03 | >0.2 · 0.1 · 0.03 | >0.2 · 0.1 · 0.03 | >0.2 · 0.1 · 0.03 | >0.2 · 0.1 · 0.03 |
| C · TRZ · RuR | >0.1 · 0.01 · 0.04 | 0.021 · 0.002 · 0.007 | 0.027 · 0.003 · 0.009 | >0.1 · 0.01 · 0.04 | 0.076 · 0.008 · 0.027 | 0.030 · 0.003 · 0.010 | 0.038 · 0.004 · 0.013 | 0.046 · 0.005 · 0.016 |
| C · CPZ · RuR | >0.1 · 0.01 · 0.04 | 0.019 · 0.002 · 0.007 | 0.023 · 0.002 · 0.008 | >0.1 · 0.01 · 0.04 | 0.039 · 0.004 · 0.014 | 0.031 · 0.003 · 0.010 | 0.041 · 0.004 · 0.013 | 0.052 · 0.005 · 0.019 |

TABLE 16-continued

Selective antibacterial effects of novel regimens without inhibition on neuroblastoma SHSY5Y cells
$IC_{50}$ (mg/ml · mg/ml · mM)

| | SHSY5Y | P. g. | UA159 | E. Coli | B. s. | P. a. | S. a. | L. r. |
|---|---|---|---|---|---|---|---|---|
| C · MF · RuR | >0.1 · 0.1 · 0.04 | 0.023 · 0.023 · 0.008 | 0.022 · 0.022 · 0.008 | >0.1 · 0.1 · 0.04 | >0.03 · 0.03 · 0.012 | 0.040 · 0.040 · 0.014 | 0.039 · 0.039 · 0.014 | 0.040 · 0.040 · 0.014 |
| E · OP · Zn | >0.1 · 0.1 · 0.03 | 0.023 · 0.023 · 0.007 | >0.1 · 0.1 · 0.03 | >0.1 · 0.1 · 0.03 | | >0.03 · 0.03 · 0.01 | >0.1 · 0.1 · 0.03 | >0.1 · 0.1 · 0.03 |
| G · OP · Zn | >0.1 · 0.1 · 0.03 | 0.022 · 0.022 · 0.007 | >0.1 · 0.1 · 0.03 | >0.1 · 0.1 · 0.03 | | >0.1 · 0.1 · 0.03 | >0.1 · 0.01 · 0.03 | >0.1 · 0.1 · 0.03 |
| T · OP · Zn | >0.1 · 0.1 · 0.03 | 0.024 · 0.024 · 0.007 | >0.1 · 0.1 · 0.03 | >0.1 · 0.1 · 0.03 | | >0.1 · 0.1 · 0.03 | >0.1 · 0.1 · 0.03 | >0.1 · 0.1 · 0.03 |
| G · GIM · Zn | >0.2 · 0.3 · 0.03 | 0.022 · 0.033 · 0.004 | 0.184 · 0.277 · 0.031 | >0.6 · 0.9 · 0.1 | | 0.192 · 0.287 · 0.032 | >0.6 · 0.9 · 0.1 | 0.443 · 0.664 · 0.074 |
| G · CC · Zn | >0.2 · 0.1 · 0.03 | 0.019 · 0.009 · 0.003 | 0.063 · 0.032 · 0.010 | >0.2 · 0.1 · 0.03 | | 0.108 · 0.054 · 0.016 | 0.103 · 0.052 · 0.015 | 0.147 · 0.074 · 0.022 |

*P. g.*, *Porphyromonas gingivalis*;
UA159, *Streptococcus mutans*;
*B. s.*, *Bacillus subtilis*;
*P. a.*, *Pseudomonas aeruginosa*;
*S. a.*, *Staphylococcus aureus*,
*L. r.*, *Lactobacillus reuteri*.
$IC_{50}$, concentrations of 50% inhibition on bacterial proliferation.

TABLE 17

Anti-proliferative effects of drug combinations on cancer cells more than on normal SG cells.

| Drugs | $IC_{50}$ (mg/ml · mg/ml · mM) | | Potency ratio |
|---|---|---|---|
| | OECM-1 cells | SG cells | |
| C · Mem · VO₄ | 0.002 · 0.005 · 0.005 | 0.009 · 0.031 · 0.031 | 6 |
| C · MF · VO₄ | 0.001 · 0.001 · 0.002 | 0.015 · 0.015 · 0.050 | 25 |
| C · CPZ · VO₄ | 0.001 · 0.001 · 0.004 | 0.007 · 0.007 · 0.023 | 6 |
| C · Eti · VO₄ | 0.001 · 0.010 · 0.003 | 0.025 · 0.254 · 0.085 | 28 |
| E · Eti · RuR | 0.047 · 0.047 · 0.006 | 0.442 · 0.442 · 0.051 | 9 |
| T · TRZ · RuR | 0.031 · 0.009 · 0.010 | 0.633 · 0.199 · 0.231 | 22 |

OECM-1, oral squamons carcinoma cells;
SG, normal oral keratinocytes.
$IC_{50}$, concentrations of 50% inhibition on cell proliferation.

What is claimed is:

1. A pharmaceutical composition (PTM) for use in antimicrobial effects against a pathogen and/or for use in management of infectious diseases, neurodegenerative diseases, dementia, diabetes, obesity, metabolic syndromes, periodontitis, dental caries, osteoporosis, cancers and/or chronic pain, comprising in therapeutically effective amounts therefor of a polyphenol (P), a clinical drug with a selective target (T) and a metal ion (M),
   wherein the polyphenol is at least one selected from the group consisting of green tea polyphenols, black tea polyphenols, curcumin, EGCG, and cinnamon,
   wherein the clinical drug with the selective target is at least one selected from the group consisting of NaF, memantine, metformin, thioridazine, chlorpromazine, tobramycin, rifampin, streptomycin, isoniazide, verapamil, diltiazem, dithiothreitol, dibucaine, digitonin, polymycin B, cisplatin, dequalinium, 4-hexylresorcinol, ursodeoxycholic acid, etidronate, glibenclamide, 3,4-diaminopyridine, tetramethylpyrazine, and nordihydroguaiaretic acid, and
   wherein the metal ion is at least one selected from the group consisting of $Cu^{2+}$, $Mn^{2+}$, $VO_4^{2+}$, $Zn^{2+}$, $Sr^{2+}$, $SeO_3^{-2}$, $Ag^+$, $Ge^{4+}$ and ruthenium red (RuR).

2. The pharmaceutical composition of claim 1, wherein the pathogen is at least one selected from the group consisting of *Porphyromonas gingivalis*, *Streptococcus mutans*, *E. coli*, *Pseudomonas aeruginosa*, *Bacillus subtilis*, *Staphytococcus aureus*, MRSA and *Mycobacterium tuberculosis*.

3. The pharmaceutical composition of claim 1, wherein the proportion between the concentration of the polyphenol and the clinical drug with the selective target is 1:0.1-3.

4. The pharmaceutical composition of claim 1, wherein an interaction between the polyphenol, the clinical drug with the selective target and the metal ion provides a synergistic therapeutic effect versus a reference composition lacking said polyphenol and/or metal ion and amounts thereof.

5. A method for treating a pathogen, infectious diseases, neurodegenerative diseases, dementia, diabetes, obesity, metabolic syndromes, periodontitis, dental caries, osteoporosis, cancers and/or chronic pain, the method comprising administering to a subject in need thereof a pharmaceutical composition of claim 1 comprising a polyphenol, a clinical drug with a selective target and a metal ion, wherein an interaction between the polyphenol, the clinical drug with the selective target and the metal ion provides a synergistic therapeutic effect versus a reference composition lacking said polyphenol and/or metal ion and amounts thereof.

6. The method of claim 5, wherein the polyphenol is at least one selected from the group consisting of tea polyphenols, curcumin, EGCG, theaflavin, apigenin, berberine, quercetin, tannin, catechin, chlorogenic acid, isoflavonc, anthocyanidin, cocoa polyphenols, citrin, tetramethylpyrazine, nordihydroguaiaretic acid, flavonoid and resveratrol.

7. The method of claim 5, wherein the clinical drug with the selective target is at least one selected from the group consisting of receptor agonists or antagonists, ion channel modulators, membrane ion transporters and mitochondrial functional modulators.

8. The method of claim 5, wherein the clinical drug with the selective target is at least one selected from the group consisting of NaF, memantine, metformin, thioridazine, chlorpromazine, tobramycin, rifampin, streptomycin, isoniazide, verapamil, diltiazem, dithiothreitol, dibucaine, digitonin, polymycin B, cisplatin, dequalinium, 4-hexylresorcinol, ursodeoxycholic acid, etidronate, glibenclamide and 3,4-diaminopyridine.

9. The method of claim 5, wherein the metal ion is at least one selected from the group consisting of $Cu^{2+}$, $Mn^{2+}$, $VO_4^{2+}$, $Zn^{2+}$, $Sr^{2+}$, $SeO_3^{-2}$, $Ag^+$ and RuR.

10. The method of claim 5, wherein the pathogen is at least one selected from the group consisting of *Porphyromonas gingivalis, Streptococcus mutans, E. coli, Pseudomonas aeruginosa, Bacillus subtilis, Staphytococcus aureus,* MRSA and *Mycobacterium tuberculosis.*

11. The method of claim 5, wherein the proportion between the concentration of the polyphenol and the clinical drug with the selective target is 1:0.1-3.

* * * * *